US008592424B2

(12) United States Patent
Aung-Din

(10) Patent No.: US 8,592,424 B2
(45) Date of Patent: Nov. 26, 2013

(54) TOPICAL REGIONAL NEURO-AFFECTIVE THERAPY

(75) Inventor: Ronald Aung-Din, Sarasota, FL (US)

(73) Assignee: Afgin Pharma LLC, Sarasota, FL (US)

( * ) Notice: Subject to any disclaimer, the term of this patent is extended or adjusted under 35 U.S.C. 154(b) by 220 days.

(21) Appl. No.: 13/000,892

(22) PCT Filed: Jun. 29, 2009

(86) PCT No.: PCT/US2009/003859
§ 371 (c)(1),
(2), (4) Date: Dec. 22, 2010

(87) PCT Pub. No.: WO2010/005507
PCT Pub. Date: Jan. 14, 2010

(65) Prior Publication Data
US 2011/0178114 A1 Jul. 21, 2011

Related U.S. Application Data

(60) Provisional application No. 61/133,475, filed on Jun. 30, 2008, provisional application No. 61/199,124, filed on Nov. 13, 2008, provisional application No. 61/199,568, filed on Nov. 18, 2008, provisional application No. 61/199,566, filed on Nov. 18, 2008.

(51) Int. Cl.
| *A01N 43/58* | (2006.01) |
| *A01N 43/60* | (2006.01) |
| *A01N 43/42* | (2006.01) |
| *A01N 43/78* | (2006.01) |
| *A01N 43/38* | (2006.01) |
| *A01N 43/06* | (2006.01) |
| *A61K 31/50* | (2006.01) |
| *A61K 31/495* | (2006.01) |
| *A61K 31/44* | (2006.01) |
| *A61K 31/425* | (2006.01) |
| *A61K 31/40* | (2006.01) |
| *A61K 31/38* | (2006.01) |
| *C07D 471/00* | (2006.01) |
| *C07D 491/00* | (2006.01) |
| *C07D 221/18* | (2006.01) |
| *C07D 277/82* | (2006.01) |
| *C07D 209/36* | (2006.01) |
| *C07D 333/12* | (2006.01) |

(52) U.S. Cl.
USPC ........... 514/250; 514/284; 514/285; 514/288; 514/367; 514/438; 544/346; 546/62; 546/75; 548/161; 548/484; 549/74

(58) Field of Classification Search
USPC ......... 514/250, 284, 285, 288, 367, 418, 438; 544/346; 546/62, 75; 548/161, 484; 549/74
See application file for complete search history.

(56) References Cited

U.S. PATENT DOCUMENTS 3,598,122 A 8/1971 Zaffaroni

| 3,797,494 A | 3/1974 | Zaffaroni |
| 4,144,317 A | 3/1979 | Higuchi et al. |
| 4,201,211 A | 5/1980 | Chandrasekaran et al. |
| 4,262,003 A | 4/1981 | Urquhart et al. |
| 4,379,454 A | 4/1983 | Campbell et al. |
| 4,511,563 A | 4/1985 | Schmolka |
| 4,588,580 A | 5/1986 | Gale et al. |
| 4,767,619 A | 8/1988 | Murray |
| 4,806,341 A | 2/1989 | Chien et al. |
| 4,816,470 A | 3/1989 | Dowle et al. |
| 4,820,720 A | 4/1989 | Sanders et al. |
| 4,861,760 A | 8/1989 | Mazuel et al. |
| 4,883,660 A | 11/1989 | Blackman et al. |
| 4,916,132 A | 4/1990 | Seibel |
| 5,016,652 A | 5/1991 | Rose et al. |
| 5,026,556 A | 6/1991 | Drust et al. |
| 5,037,845 A | 8/1991 | Oxford |
| 5,053,227 A | 10/1991 | Chiang et al. |
| 5,069,909 A | 12/1991 | Sharma et al. |
| 5,307,953 A | 5/1994 | Regan |
| 5,318,780 A | 6/1994 | Viegas et al. |
| 5,364,628 A | 11/1994 | Kissel et al. |
| 5,466,699 A | 11/1995 | Robertson et al. |
| 5,521,196 A | 5/1996 | Audia et al. |
| 5,545,644 A | 8/1996 | Macor et al. |
| 5,554,639 A | 9/1996 | Craig et al. |
| 5,562,917 A | 10/1996 | Durif et al. |

(Continued)

FOREIGN PATENT DOCUMENTS

| EP | 0303507 | 2/1989 |
| EP | 0500086 | 8/1992 |
| EP | 0636623 | 2/1995 |
| EP | 0705600 | 10/1996 |
| WO | 9118897 | 12/1991 |
| WO | 9206973 | 4/1992 |
| WO | 9426270 | 1/1994 |
| WO | 9505137 | 2/1995 |
| WO | 03/024456 | 3/2003 |
| WO | 03/032983 | 4/2003 |
| WO | 2004/112723 | 12/2004 |
| WO | WO 2007128462 A1 * | 11/2007 |

OTHER PUBLICATIONS

Katzenschlager et. al., Movement Disorders, 2005, Movement Disorder Society, vol. 20, No. 2, pp. 151-157.*
Merello et. al., Journal of Neurology, Neurosurgery, and Psychiatry, 1994, BMJ Publishing Group, vol. 57, pp. 1503-1509.*
Trojanowski et. al., Annals of the New York Academy of Sciences, 2003, New York Academy of Sciences, vol. 991, pp. 107-110.*
CAS STN abstract; Reches et. al., Advances in Neurology, 1984, vol. 40, pp. 171-179.*
Cousins et. al., European Journal of Pharmacology, 1997, Elsevier, vol. 322, pp. 137-145.*

(Continued)

*Primary Examiner* — Sarah Pihonak
(74) *Attorney, Agent, or Firm* — Davidson, Davidson & Kappel, LLC

(57) ABSTRACT

A method of treating a disease state or condition in humans via topical brainstem afferent stimulation therapy via the administration of a drug to the back of the neck of a human patient at the hairline in close proximity to and under or on the area of skin above the brain stem to provide regional neuro-affective therapy is disclosed.

17 Claims, No Drawings

(56) References Cited

U.S. PATENT DOCUMENTS

| | | |
|---|---|---|
| 5,698,571 A | 12/1997 | Audia et al. |
| 5,705,520 A | 1/1998 | Craig et al. |
| 5,719,197 A | 2/1998 | Kanios et al. |
| 5,807,571 A | 9/1998 | List |
| 5,814,653 A | 9/1998 | Flaugh et al. |
| 5,837,289 A | 11/1998 | Grasela et al. |
| 5,855,907 A | 1/1999 | Peyman |
| 5,863,559 A | 1/1999 | Phillips et al. |
| 5,863,935 A | 1/1999 | Robertson et al. |
| 5,872,145 A | 2/1999 | Plachetka |
| 6,020,001 A | 2/2000 | Phillips et al. |
| 6,060,499 A | 5/2000 | Plachetka |
| 6,103,266 A | 8/2000 | Tapolsky et al. |
| 6,197,331 B1 | 3/2001 | Lerner |
| 6,368,627 B1 | 4/2002 | Phillips et al. |
| 6,383,471 B1 | 5/2002 | Chen et al. |
| 6,384,034 B2 | 5/2002 | Simitchieva et al. |
| 6,455,557 B1 | 9/2002 | Pellegrini et al. |
| 2002/0132827 A1* | 9/2002 | Nichols et al. ............... 514/311 |
| 2003/0013753 A1 | 1/2003 | Aung-Din |
| 2003/0167556 A1 | 9/2003 | Kelley et al. |
| 2004/0220205 A1 | 11/2004 | Wikstrom |
| 2007/0065463 A1 | 3/2007 | Aung-Din |
| 2007/0203209 A1 | 8/2007 | Bartolini et al. |
| 2007/0275964 A1 | 11/2007 | Griffith et al. |
| 2008/0038363 A1 | 2/2008 | Zaffaroni et al. |

OTHER PUBLICATIONS

Messlinger, K; Hotta, H.; Pawlak, M.; Schmidt, R.F., Effects of the 5-HT1 receptor agonists, sumatriptan and CP 93,129, on dural arterial flow in the rat, *Eur J Pharmacol*, vol. 332 No. 2, Aug. 6, 1997 pp. 173-181.

Piovesan, et al., "Referred Pain After Painful Stimulation of the Greater Occipital Nerve in Humans: Evidence of Convergence of Cervical Afferences on Trigeminal Nuclei", *Cephalalgia*, 2001, 21, 107-109.

Rougier, et al. In vivo percutaneous penetration of some organic compounds related to anatomic site in humans; predictive assessment by the stripping method, J. Pharmac. Sci., vol. 76, No. 6, Jun. 1987, pp. 451-454.

Goodman & Gilman, The Pharmacological Basis of Therapeutics, Ninth Edition, (1996), Chapter 21, Peroutka, Drugs Effective in the Therapy of Migraine, pp. 487-502.

Methods Find Exp Clin Pharmacol 2002, 24(6): 371-391—Gateways to Clinical Trials—Jul.-Aug. 2002 M. Bayes, X. Rabasseda, J.R. Prous.

Schwarz, et al., Postdural Puncture Headache: Diagnosis, Prevention and Therapy Schmerz, vol. 13, No. 5, 1999—pp. 332-340; Abstract.

Aung-Din, Ronald, Transdermal Sumatriptan: A Novel Dosage Form Efficacious in the Treatment of Acute Migraine, Headache: The Journal of Head and Face Pain, vol. 45, No. 5, pp. 389-390, May 2002.

Aung-Din, Ronald, Transdermal Sumatriptan in Clinical Practice: The Experience of 42 Patients with Acute Migraine in an Outpatient Setting, Headache: The Journal of Head and Face Pain, vol. 43, No. 5, p. 523, May 2003.

Aung-Din, Ronald and Kinnard, Fred, Topical Tizanidine (Zanaflex) Gel Effective in Migraine and Tension-Type Headache, Headache: The Journal of Head and Face Pain, vol. 44, No. 5, p. 509, May 2004.

Norton, Patrice G.W., Transdermal Sumatriptan May Relieve Migraines, Internal Medicine News, vol. 36, Issue 19, p. 14, Oct. 1, 2003.

Aung-Din, R. et al, Transdermal sumatriptan:effectiveness and convenience in migraineurs, Blackwell Science Ltd. Cephalalgia, 2001, 21, 412.

Bartsch, T. and Goadsby P.J., "Increased responses in trigeminocervical nociceptive neurons to cervical input after stimulation of the dura mater", Brain, vol. 126, No. 8, 1801-1813, Aug. 2003; Abstract.

Bogduk, Nikolai, MD, PhD, "Cervicogenic Headache: Anatomic Basis and Pathophysiologic Mechanisms", Current Pain and Headache Reports 2001, 5:382.

Aung-Din, Ronald, MD, "Topical Delivery: Topical Regional Neuro-Affective (TRNA) Therapy: Novel Ground-Breaking Triptan Drug Delivery for Treating Migranes", Drug Delivery Technology, Sep. 2009, vol. 9, No. 8.

Pierce, Mark et al, "Zelrix: a novel transdermal formulation of sumatriptan" Headache, vol. 49, Jun. 2009, pp. 817-825; Abstract.

Patel, SR et al, "Controlled non-invasive transdermal iontophoretic delivery of zolmitriptan hydrochloride in vitro and in vivo" Eur. J. Pharm. And Biopharm, vol. 72, Feb. 2009, pp. 304-309; Abstract.

Garg, T et al, "Elastic liposomal formulation for sustained delivery of antimigraine drug: In vitro characterization and biological evaluation" Drug Dev. Ind. Pharm.., vol. 34, Oct. 2008, pp. 1100-1110; Abstract.

Tennant, F., "Topical Use of Morphine", Practical Pain Management, Oct. 2008, pp. 42-43.

Office Action dated Aug. 1, 2007 issued in corresponding U.S. Appl. No. 10/163,234.

Applicant's Response to Office Action dated Jan. 19, 2007 filed in corresponding U.S. Appl. No. 10/163,234.

Office Action dated Sep. 21, 2006 issued in corresponding U.S. Appl. No. 10/163,234.

Applicant's Response to Office Action dated Mar. 15, 2006 issued in corresponding U.S. Appl. No. 10/163,234.

Office Action dated Nov. 17, 2005 issued in corresponding U.S. Appl. No. 10/163,234.

Applicant's Response to Office Action dated Aug. 18, 2005 filed in corresponding U.S. Appl. No. 10/163,234.

Office Action dated May 4, 2010 issued in corresponding U.S. Appl. No. 11/999,093.

Applicant's Response to Office Action dated Jan. 6, 2010 filed in corresponding U.S. Appl. No. 11/999,093.

Office Action dated Oct. 27, 2009 issued in corresponding U.S. Appl. No. 11/999,093.

Applicant's Response to Office Action dated May 19, 2009 filed in corresponding U.S. Appl. No. 11/999,093.

Office Action dated Mar. 19, 2009 issued in corresponding U.S. Appl. No. 11/999,093.

Applicant's Response to Office Action dated Dec. 12, 2008 filed in corresponding U.S. Appl. No. 11/999,093.

Applicant's Response to Office Action dated Oct. 12, 2008 filed in corresponding U.S. Appl. No. 11/999,093.

Office Action dated Jun. 23, 2008 issued in corresponding U.S. Appl. No. 11/999,093.

Office Action dated Mar. 14, 2011 issued in corresponding U.S. Appl. No. 10/560,889.

Applicant's Response to Office Action dated Dec. 10, 2010 filed in corresponding U.S. Appl. No. 10/560,889.

Office Action dated Jun. 11, 2010 issued in corresponding U.S. Appl. No. 10/560,889.

International Search Report and Written Opinion issued in connection with International Application No. PCT/US09/03859 mailed on Aug. 21, 2009.

Chepyala et al., Treatment of Cyclic Vomiting Syndrome, Current Treatment Options in Gastroenterology, 2007, 10: abstract.

Remington's Pharmaceutical Sciences, 15th Edition, 1975, Mack Publishing Co. p. 1529.

* cited by examiner

TOPICAL REGIONAL NEURO-AFFECTIVE THERAPY

This application is a national phase application under 35 U.S.C. §371 of International Application No. PCT/US2009/003859, filed Jun. 29, 2009, which claims priority to U.S. Provisional Patent Application No. 61/133,475, filed Jun. 30, 2008; U.S. Provisional Patent Application No. 61/199,124 filed Nov. 13, 2008; U.S. Provisional Patent Application No. 61/199,568, filed Nov. 18, 2008; and U.S. Provisional Patent Application No. 61/199,566, filed Nov. 18, 2008.

FIELD OF THE INVENTION

The invention relates to topical regional neuro-affective therapy ("TRNA THERAPY") for the treatment of neuronal hyperexcitability and neurochemical dysfunction syndromes. This is accomplished via administration of effective amounts of these agents at the back of the neck at the hairline ("BONATH").

BACKGROUND OF THE INVENTION

The approximate 2½ pound human brain is comprised of the most complex material known to man. The neuron, the primary functional cell of the nervous system, operates on the basis of electrical impulses that result in the release of neurochemical substances (neurotransmitters) at specific receptors: dopamine, serotonin, acetylcholine, norepinephrine, gamma-amino butyric acid (GABA), and many others. There are estimated to be 80-100 billion (10 times the world population) neurons in the average human brain. These neurons, in turn, make 200-300 billion coded connections with other neurons to accomplish the complex tasks of the human body.

The brainstem serves as the vital pathway for relay and processing of neural impulses flowing continuously between the brain and the rest of the body. It is about the size of the thumb and contains the most dense and complicated wiring systems in the human body. In addition to the axons and dendrites (wires) that carry nerve impulses, the brainstem also contains critical nuclei that function as electrical generators and relays. Some of the nuclei are related to cranial nerve function while others serve as generators and impulse centers for pain perception, the autonomic system "fight or flight" response, wakefulness and alertness, as well as cardio-respiratory and related autonomic functions.

In the prior art, there have been previous attempts to provide for a more efficacious and safe treatment using serotonin agonists specific for the 5-HT1 receptor subtype.

For Example, U.S. Pat. No. 5,863,935 to Robertson et al. describes certain compounds having "5-HT1-like" receptor agonist properties and their administration in a number of ways, including topical or intranasal application.

Additionally, U.S. Pat. No. 5,805,571 to List, describes a transdermal therapeutic system for the systemic administration of active substances wherein at least one of the active substances listed is a serotonin agonist of the group comprising indole derivatives. Typically, transdermal systems are not used in acute situations because they do not provide an immediate effect, but rather provide prophylaxis or prolonged effect through their sustained delivery process. Transdermal systems such as that described in the '571 patent to List require a period of time for the drug to pass through a barrier layer and onto/into the skin (ionophoresis through concentrations gradients) which may take e.g., a substantial period of time until the dose of drug that is absorbed is sufficient to alleviate the pain associated with the headache. These previously described transdermal systems require the operation of a concentration gradient for the absorption of topically applied drug to enter the bloodstream through the small blood vessels in the skin and soft tissues. After entry into the systemic circulation in sufficient quantity to establish a therapeutic level, drug is eventually delivered by the cerebral blood flow to the target sites. Accordingly, this process involves relative considerable time, not amenable for the acute relief of symptoms. Furthermore, it is influenced by such factors as cardiac output and cerebrovascular disease that influence blood flow and tissue absorption.

The inventor has previously described the delivery of anti-migraine drugs (e.g., triptans and ergot alkaloids) and muscle relaxants (e.g., tizanidine) through topical regional neuro-affective (TRNA) therapy by topical application (e.g., as a cream/gel or a sustained release patch) applied at the back of the neck at the hairline (BONATH). The author has demonstrated the efficacy of this route of delivery for the treatment of migraine, another brainstem disorder, using sumatriptan and tizanidine compounded in an appropriate dermal penetration enhancing medium.

The inventor's previous U.S. Patent Publication No. 20030013753 (filed Jun. 5, 2002) and U.S. Patent Publication No. 20080090894, both of which are hereby incorporated by reference, disclose a unit dose of a topical formulation for treating a migraine or cluster headache comprising: a serotonin agonist incorporated into a pharmaceutically acceptable vehicle for topical administration onto the skin of a human patient. Preferably, the unit dose providing the serotonin agonist is in a form that is immediately absorbable when said unit dose is applied onto human skin. Preferably, the serotonin agonist comprises from about 0.5 to about 200 mg of sumatriptan, by weight based on the succinate salt, or a therapeutic equivalent dose of another topically absorbable pharmaceutically acceptable serotonin agonist. Preferably, the unit dose provides relief from a migraine or cluster headache within about 2 hours after topical administration to a human patient.

The inventor's previous U.S. Patent Publication No. 20070065463 (filed Jun. 21, 2004) discloses a topical formulation for treating migraines or cluster headaches, muscle sprains, muscle spasms, spasticity, tension headaches, tension related migraines and related conditions associated with muscle tension and pain comprising: a therapeutically effective amount of an active agent(s) incorporated into a pharmaceutically acceptable excipient for topical administration onto the skin of a human patient, the active agent(s) being selected from the group consisting of: i) an ergot alkaloid; ii) a skeletal muscle relaxant; or iii) a combination of an ergot alkaloid and a skeletal muscle relaxant; the active agent(s) being present in an effective concentration such that a unit dose of the topical formulation provides a therapeutic effect within about 2 hours after topical administration to the human patient. In certain preferred embodiments, the topical formulation comprises a skeletal muscle relaxant such as tizanidine. In certain preferred embodiments, the unit dose comprises from about 0.4 mg to 8 mg, preferably from about 0.2 mg to about 4 mg of tizanidine hydrochloride.

In instances where humans suffer from conditions involving neuronal hyperexcitability and/or a neurochemical dysfunction syndrome(s), adequate treatment is not generally available. Such conditions include headache including migraine, cluster, tension-type headache and the related menstrual conditions of menstrual migraine. In fact, other such conditions include, but are not limited to, pain, anxiety reactions, panic attacks, seizures of both epileptic and non-epileptic (psychogenic) varieties; and acute head and face pain syndromes such as trigeminal neuralgia, atypical facial pain, occipital neuralgia, TMJ related pain, hot flashes, menstrual associated dysphoria, Multiple Sclerosis, and Parkinson's Disease and similar or related syndromes.

For example, Parkinson's disease is a common, debilitating, neurological condition of unknown cause. There is no known cure and treatment is directed at reducing symptoms. It is considered the result of a progressive degenerative process within the central nervous system (CNS). A significant reduction in brain levels of the neuro-chemical dopamine is the hallmark characteristic of the disease process. Other brain chemicals are also affected. Pathological studies indicate death and loss of dopamine producing cells within the substantia nigra of the brainstem. Loss of cells in the caudate and putamen (the striatum) which rely on dopamine connections from substantia nigra, the ascending nigra-striatal dopaminergic pathway, also occurs. The resultant cardinal clinical signs of Parkinson's disease are: tremor, postural instability, bradykinesia/rigidity. Depression, autonomic dysfunction, and memory disturbance/cognitive problems are also common. Parkinson's disease is the third most common outpatient neurological diagnosis after headaches and seizures.

The mainstay treatment of Parkinson's disease is aimed at normalizing the reduced central dopamine levels. This is accomplished by either providing exogenous levodopa orally for eventual conversion into dopamine in the brain or the use of dopamine agonists to augment the endogenous dopamine. COMT inhibitors are also used in the therapeutic regimen to reduce the breakdown of dopamine, allowing for higher and more persistent levels at the receptors. The problem with these traditional therapies is that they are unable to provide the stable dopamine levels at the receptors which occur in the natural state. The fluctuations in dopamine levels result in fluctuations in clinical function: so called "on and off" states. They also affect dopamine receptor sensitivity in the long term such that "motor complications" and dyskinesias may occur after several years of therapy. This is particularly true with exogenous dopamine therapy and in patients diagnosed in their younger years.

Patients with end-of-dose wearing off phenomena, the most significant of which is "freezing", where one is essentially paralyzed and unable to move, are significantly affected in their activities from the sudden episodic dopamine deficiency at the receptor level.

Apomorphine hydrochloride (Apokyn by Vernalis, which was recently acquired by Ipsen Pharmaceuticals) is given as subcutaneous injections to counter such "off periods". It has also been administered via intra-peritoneal infusion. The drug is reported to take effect within 10-15 minutes and last for up to 1½ hours. This allows a patient to engage in pre-planned activities that would otherwise not have been pursued—going out to dinner, etc. The resultant sense of control over one's disease and associated reduced anxiety for such affected patients is immeasurable. Apokyn is marketed for use in the treatment of "acute, intermittent treatment of hypomobility, off episodes (end-of-dose wearing off and unpredicatable on/off episodes) associated with advanced Parkinson's disease".

Unfortunately, as an injection, Apokyn has not been a preferred form of treatment despite its efficacy. It is also associated with a relative high cost (approximately $100 for a 3 ml cartridge) not affordable for routine use by most patients. It involves a titration phase for tolerability and efficacy determination (2 mg or 0.2 ml to 6 mg or 0.6 ml) with a nurse at a doctor's office, further contributing to cost and time. Finally, Apokyn is associated with significant nausea and vomiting to the extent patients are required to take an anti-emetic (tri-methobenzamide/Tigan 200-300 mg 3×/day) for 3 days prior to the first injection and encouraged to continue the regimen for an additional 6 weeks. Despite using Tigan, a significant number of patients still experience nausea and vomiting—31% and 11% respectively in reported clinical trials. Other anti-emetics with anti-dopaminergic actions are contraindicated as they may worsen the symptoms of Parkinson's. Further, the requirement of medications to counter side-effects contributes to additional drug-drug interactions. Parkinson's patients are generally already on a significant degree of "polypharmacy".

The significant nausea and vomiting associated with apomorphine in oral and injectible forms is likely the result of its direct effect on the "chemoreceptor zone" of the area postrema in the floor of the IVth ventricle adjacent to the brainstem. Other commonly reported adverse events in clinical trials also indicate stimulation of other brainstem structures, including the autonomic nervous system, by the apomorphine in the cerebral brood: dizziness, yawning, somnolence, rhinorrhea, sweating, flushing, pallor, hallucinations, edema, and chest pain.

Thus, in spite of its effectiveness and potential to improve the lives of persons affected by Parkinson's disease, for the above noted reasons, the use of injectable apomorphine has been limited. Oral forms have not been pursued as they are even less well tolerated as the dose requirements are high. Intra-peritoneal and intravenous injections are impractical.

Apomorphine hydrochloride is a non-ergoline dopamine agonist that is lipophilic and soluble in water at 80 degrees Celsius. In vitro tests show it has a high affinity for the D4 dopamine receptor and moderate for the D2, D3, and D5 receptors. It also has moderate affinity for some alpha-adrenergic receptors. It has a low affinity for the dopamine D1 and serotonin receptors. Although the precise mechanism of action of apomorphine is unknown, it is believed to work through the stimulation of post-synaptic dopamine D2 receptors in the striatum, the caudate and putamen.

The significant nausea and vomiting associated with apomorphine in oral and injectible forms is likely the result of its direct effect on the "chemoreceptor zone" of the area postrema in the floor of the IVth ventricle adjacent to the brainstem. Other commonly reported adverse events in clinical trials also indicate stimulation of other brainstem structures, including the autonomic nervous system, by the apomorphine in the cerebral blood: dizziness, yawning, somnolence, rhinorrhea, sweating, flushing, pallor, hallucinations, edema, and chest pain.

For the above reasons, despite its efficacy and potential to improve the lives of persons affected by Parkinson's disease, the use of injectable apomorphine has been limited. Oral forms have not been pursued as they are even less well tolerated as dose requirements are high. Intra-peritoneal and intravenous injections are impractical but have been pursued. Intra-peritoneal apomorphine via continuous infusion pump (such as for insulin), is used in Europe.

SUMMARY OF THE INVENTION

It is an object of the present invention to provide a method of treatment in humans with topical brainstem deafferentation therapy via the regional administration of a compound useful for the treatment of such diseases or conditions that may be treated via such therapy.

It is an object of the present invention to provide a method for the treatment of neuronal hyperexcitability and neuro-chemical dysfunction syndromes including but not limited to pain, anxiety reactions, panic attacks, seizures of both epileptic and non-epileptic (psychogenic) varieties; and acute head and face pain syndromes such as trigeminal neuralgia, atypical facial pain, occipital neuralgia, TMJ related pain, hot flashes, menstrual associated dysphoria, Multiple Sclerosis, and Parkinson's Disease and similar or related syndromes.

It is an object of the invention to provide a topical formulation of a dopamine agonist(s) useful in the treatment of Parkinson's disease and/or related syndromes/diseases.

It is a further object of the invention to provide a method of treatment of Parkinson's disease and related syndromes/diseases via the topical administration of one or more dopamine agonists.

It is a further object of the invention to provide a topical formulation of a dopamine agonist(s) useful in the treatment of Parkinson's disease and/or related syndromes/diseases.

It is a further object of the invention to provide a method of treatment of impotence with erectile dysfunction in men via the topical administration of one or more dopamine agonists.

It is a further object of the present invention to provide a method for the treatment of neuronal hyperexcitability and neurochemical dysfunction syndromes in humans suffering from Parkinson's disease and/or related syndromes/diseases via topical brainstem afferent stimulation therapy via the regional administration of a compound useful for the treatment of such diseases or conditions that may be treated via such therapy.

It is a further object of the present invention to provide a method of treatment of impotence/erectile dysfunction in men and/or related syndromes/diseases via topical brainstem afferent stimulation therapy via the regional administration of a compound useful for the treatment of such diseases or conditions that may be treated via such therapy.

The above objects and others are attained by virtue of the present invention, which is directed in part to a method of treating a disease state or condition in humans via transdermal regional neuro-affective (TRNA) or regional neuro-affective (RNA) therapy via administration of a drug at the back of the neck at the hairline (BONATH). The drug is selected from, e.g., an anti-epileptic, an anxiolytic, a neuroleptic, an anti-psychotic, an analgesic, an anti-inflammatory, an anti-Parkinson's disease/syndrome drug, a sexual dysfunction drug, a drug for the treatment of dystonia, a drug for the treatment of spastic conditions, a drug for the treatment of benign essential/familial tremor, a drug for the treatment of tremor related to MS, a drug for the treatment of chronic encepahalopathies, a drug for the treatment of congenital CNS degeneration conditions/cerebral palsy, a drug for the treatment of cerebellar degeneration syndromes, a drug for the treatment of neuropathic and/or neurogenic pain, a drug for smoking cessation, a drug for appetite suppression, a drug for neurodegenerative conditions, a drug for the treatment of multiple sclerosis, a drug for the treatment of insomnia, a drug for the treatment of fatigue, a drug for the treatment of vertigo, nausea and/or dizziness, a drug for the treatment of writer's cramp and restless leg syndrome, a drug for the treatment of ADD/ADHD, and other drugs which can beneficially be administered at the back of the neck at the hairline in close proximity to and under or on the area of skin above the brain stem to provide regional neuro-affective therapy to the patient.

The invention is also directed to a topical formulation, comprising a drug selected from an anti-epileptic, an anxiolytic, a neuroleptic, an anti-psychotic, an analgesic, an anti-inflammatory, an anti-Parkinson's disease/syndrome drug, a sexual dysfunction drug, a drug for the treatment of dystonia, a drug for the treatment of spastic conditions, a drug for the treatment of benign essential/familial tremor, a drug for the treatment of tremor related to MS, a drug for the treatment of chronic encepahalopathies, a drug for the treatment of congenital CNS degeneration conditions/cerebral palsy, a drug for the treatment of cerebellar degeneration syndromes, a drug for the treatment of neuropathic and/or neurogenic pain, a drug for smoking cessation, a drug for appetite suppression, a drug for neurodegenerative conditions, a drug for the treatment of multiple sclerosis, a drug for the treatment of insomnia, a drug for the treatment of fatigue, a drug for the treatment of vertigo, nausea and/or dizziness, a drug for the treatment of writer's cramp and restless leg syndrome, a drug for the treatment of ADD/ADHD, and combinations of any of the foregoing, in a formulation suitable for administration at the the back of the neck at the hairline in close proximity to and under or on the area of skin above the brain stem of a human patient to provide regional neuro-affective therapy to the patient. The topical formulation may be prepared as an immediate, controlled or sustained release formulation.

The drug formulations useful in the present invention may be in a form selected from a topical formulation (e.g, a cream, ointment or gel); a transdermal device; or an implantable or injectable formulation.

The invention is further directed to the use of a drug selected from the group consisting of anti-epileptic, an anxiolytic, a neuroleptic, an anti-psychotic, an analgesic, an anti-inflammatory, an anti-Parkinson's disease/syndrome drug, a sexual dysfunction drug, a drug for the treatment of dystonia, a drug for the treatment of spastic conditions, a drug for the treatment of benign essential/familial tremor, a drug for the treatment of tremor related to MS, a drug for the treatment of chronic encepahalopathies, a drug for the treatment of congenital CNS degeneration conditions/cerebral palsy, a drug for the treatment of cerebellar degeneration syndromes, a drug for the treatment of neuropathic and/or neurogenic pain, a drug for smoking cessation, a drug for appetite suppression, a drug for neurodegenerative conditions, a drug for the treatment of multiple sclerosis, a drug for the treatment of insomnia, a drug for the treatment of fatigue, a drug for the treatment of vertigo, nausea and/or dizziness, a drug for the treatment of writer's cramp and restless leg syndrome, a drug for the treatment of ADD/ADHD, in the preparation of a medicament for providing regional neuro-affective therapy to a human patient, wherein the drug is administered at the back of the neck at the hairline in close proximity to and under or on the area of skin above the brain stem to provide regional neuro-affective therapy to the patient.

In certain embodiments, the drug is applied to the posterior cervical region of the human in order to effect the brainstem afferent stimulation therapy. Most preferably, the topical formulation or transdermal therapeutic system is applied to the back of the neck, preferably in close proximity to or on the area of skin above the brain stem.

In other embodiments, the drug is administered via implantation or injection at the back of the neck at the hairline (BONATH). In such embodiments, the therapy is accomplished via the availability of the drug(s) at the free nerve endings under the epidermis. In such embodiments, the drug may be incorporated into an implantation device or may be incorporated into a carrier such as a gel or matrix that will provide a prolonged release/effect of the dopamine agonist at the site. The carrier may be a hydrophilic or hydrophobic material, a colloidal material, and may be in a state ranging from a viscous liquid to a solid polymeric insert.

Certain embodiments of the invention are directed to a method of treatment, comprising delivering a drug(s) through regional neuro-affective therapy by application as a cream/gel or a sustained release patch applied at the back of the neck at the hairline (BONATH), or via administration under the skin at the BONATH via an implantable or injectable drug formulation or device.

In certain embodiments, the method further provides for a therapeutically effective treatment through transdermal regional neuro-affective (TRNA) therapy by application of a drug(s) as a cream/gel or a sustained release patch applied at the back of the neck at the hairline (BONATH) without the side-effects and the other draw-backs of the current injection method.

In certain embodiments, the drug is a dopamine agonist such as apomorphine (Apokyn®, APO-Go®), pramipexole (Mirapexin®), ropinirole (Requip®), bromocriptine (Parlodel®), cabergoline (Cabaser®, Dostinex®), pergolide (Permax®, Celance®) rotigotine (Neupro®), mixtures of any of the foregoing, or other dopamine agonists known to those skilled in the art.

In other embodiments, the drug is opioid such as morphine, codeine, dihydrocodeine, hydrocodone, hydromorphone, nicomorphine, oxycodone, oxymorphone, fentanyl, alphamethylfentanyl, alfentanil, sufentanil, remifentanil, carfentanyl, ohmefentanyl, thebaine, oripavine, diacetylmorphine (heroin), phenylpiperidines such as pethidine (meperidine) and ketobemidone, allylprodine, prodine, propoxyphene, dextropropoxyphene, dextromoramide, bezitramide, piritramide, methadone, dipipanone, levomethadyl Acetate (LAAM), loperamide, diphenoxylate, dezocine, pentazocine, phenazocine, buprenorphine, dihydroetorphine, etorphine, butorphanol, nalbuphine, levorphanol, levomethorphan, lefetamine, meptazinol, tilidine, tramadol, tapentadol, mixtures thereof, and the like.

In yet other embodiments, the drug is Tarpentadol (a centrally acting oral analgesic having two mechanisms of action combining mu-opioid receptor agonism and norepinephrine reuptake inhibition).

Alternatively, the drug is an opioid antagonist, for example, naloxone, naltrexone, nalmefene, or mixtures thereof.

In yet other embodiments, the drug is a selective norepinephrine reuptake inhibitor, such as Atomoxetine (Strattera®), Mazindol (Mazanor®, Sanorex®), Nisoxetine (LY-94939), Reboxetine (Edronax®, Vestra®), Viloxazine (Vivalan®), Mixtures thereof, and the like.

In yet other embodiments, the drug is a benzodiazepine, such as lorazepam (Ativan®), diazepam (Valium®), clonazepam (Klonopin®), chlordiazepoxide (Librium®), alprazolam (Xanax®), mixtures thereof, and the like. In other embodiments, the drug is a neuroleptic or psychotropic such as chlorpromazine (Thorazine®), haloperidol (Haldol®), risperidone (Risperdal®), olanzapine (Zyprexa®) and quetiapine (Seroque®).

In yet other embodiments, the drug is a norepinephrine-dopamine reuptake inhibitor (NDRI), such as Amineptine (Survector®), Bupropion (Wellbutrin®, Zyban®), Dexmethylphenidate (Focalin®), Methylphenidate (Ritalin®, Concerta®), Nomifensine (Mental®), mixtures thereof, and the like.

In yet other embodiments, the drug is a serotonin-norepinephrine reuptake inhibitor (SNRI), such as Desvenlafaxine (Pristiq®), Duloxetine (Cymbalta®), Milnacipran (Ixel®, Savella®), Venlafaxine (Effexor®), mixtures thereof, and the like.

In yet other embodiments, the drug is a tricyclic antidepressant (TCA), such as Amitriptyline (Elavil®), Butriptyline (Evadene®, Evadyne®), Clomipramine (Anafranil®), Desipramine (Norpramin®, Pertofrane®), Dosulepin (Prothiade®), Doxepin (Adapin®, Sinequan®), Imipramine (Tofranil®), Lofepramine (Feprapax®, Gamanil®, Lomont®), Nortriptyline (Aventyl®, Nortrilen®, Pamelor®), Protriptyline (Vivactil®), Trimipramine (Surmontil®), mixtures thereof, and the like.

In yet other embodiments, the drug is a tetracyclic antidepressant, such as Amoxapine (Asendin®), Maprotiline (Ludiomil®), Mianserin (Tolvon®), mixtures thereof, and the like.

In yet other embodiments, the drug is an atypical antipsychotic, such as Ziprasidone (Geodon®, Zeldox®), Nefazodone (Serzone®), and the like.

In yet other embodiments, the drug is an anti-epileptic drug such as Valproic acid (Depacon®/Depalcote®), Leviteracetem (Keppra®), Lamotrigene (Lamictal®), Topiramate (Topamax®), Pregabalin (Lyrica®), Gabapentin (Neurontin®), Carbamazepine (Tegretol®), Oxcarbazepine (Trileptal®), Phenobarbital and other barbiturates, Tiagabine (Gabatril®), Retigabine™ (Valeant Pharmaceuticals). Lacosamide™ (Schwarz Biosciences), and Perampanel™ (Eisai) are in development as anti-epileptics and neuromodulators for other associated neurological, pain, and psychiatric conditions, and thus are further examples of potentially useful drugs in the present invention.

In yet other embodiments, the drug is an analgesic/anti-inflammatory agent such as acetaminophen; prednisone, solumedrol, and other steroids; naproxen, aspirin, voltaren, ketoprofen, ibuprofen, and other NSAID's.

In yet other embodiments, the drug is an appetite suppressant, such as Sibutramine (Meridia®, Reductil®), which is a centrally acting serotonin-norepinephrine reuptake inhibitor that is structurally related to amphetamines but having a distinct mechanism of action. Other potentially useful drugs for anti-obesity include Rimonabant (Acomplia®), substances related to amphetamine, such as phentermine and/or fenfluramine and/or dexfenfluramine, (the combination popularly referred to phenfen) may also be useful in the treatments of the present invention. It is believed that the present method of treatment would avoid the potential heart value damage found with these combinations when administered orally.

For purposes of the present invention, a "topical formulation" includes, for example, ointments, creams, lotions, pastes, gels, etc., which releases one or more drugs (e.g., dopamine agonists) at a predetermined rate over a defined period of time to a defined site of application.

For purposes of the present invention, an "injectable" formulation includes, for example, an injectable solution, suspension, gel or the like and may be in immediate release form or may provide a controlled or sustained release of the drug at the site of administration.

For purposes of the present invention, an "implantable" formulation includes, for example, a solid, semisolid or liquid drug formulation which can be administered at the site of administration (e.g., BONATH) either via injection and/or via surgical implantation. The solid may comprise microspheres, microcapsules, pellets, discs, and the like. The implantable formulations of the invention may provide a controlled or sustained release of the drug at the site of administration.

For purposes of the present invention, a "transdermal therapeutic system" is defined as a drug-containing device (including e.g., patch, disc, etc.) which releases one or more drugs at a predetermined rate over a defined period of time to a defined site of application.

For purposes of the present invention, "transdermal" delivery is the delivery by passage of a drug through the skin and into the bloodstream ("traditional" transdermal delivery) and is termed "transdermal systemic drug delivery (TSD) therapy).

For purposes of the present invention, the term "topical transdermal therapy" is synonomous with the more accurately termed topical regional neuro-affective therapy (or "TRNA therapy"). This term describes important aspects of this delivery method: topical, regional (near brainstem and cervical spinal cord), and affecting the free nerve endings of the afferent nervous system.

For purposes of the present invention "therapeutically effective" or "effective" amount is meant to be a nontoxic but sufficient amount of a compound to provide the desired therapeutic effect, e.g., avoidance of the onset of a migraine and or increased alleviation of the migraine and/or cluster headache. In the present case, for example, it is the dose of serotonin agonist that will be effective in relieving symptoms of the migraine or cluster headache. An "effective" amount of a permeation enhancer as used herein, for example, means an amount that will provide the desired increase in skin permeability and, correspondingly, the desired depth of penetration, rate of administration, and amount of drug to be delivered.

For purposes of the present invention, the term "delivers" when used with respect to the topical formulation or transdermal therapeutic system means that the formulation or system provides a mean relative release rate or flux of the drug out of the formulation or system and through the skin of the patient.

By "predetermined area of skin" is intended a defined area of intact unbroken living skin. In certain embodiments of the present invention, the predetermined area will be in the range of about 1 cm2 to about 100 cm2, preferably in the range of about 10 cm2 to about 100 cm2, more preferably in the range of about 20 cm2 to about 60 cm2. However, it will be appreciated by those skilled in the art of topical delivery that the area of skin through which drug is administered may vary significantly, depending on the formulation, dose, the application of the formulation, and the like.

"Penetration enhancement" or "permeation enhancement" for purposes of the present invention relates to an increase in the permeability of skin to a pharmacologically active agent, i.e., so as to increase the rate at which the drug permeates through the skin and enters the bloodstream. The enhanced permeation effected through the use of such enhancers can be observed by measuring the rate of diffusion of drug through animal or human skin using a diffusion cell apparatus.

For purposes of the present invention, the "brainstem afferent stimulation therapy region" is defined as the skin region of the head and/or at the frontotemporal region and/or upper posterior cervical area. In certain preferred embodiments, the treatment area is the post cervical area in close proximity to the brain stem. Preferably this area is a relatively hairless area of the patient's head and/or neck.

For purposes of the present invention, the drug may be in the form of the base, or may be provided as a pharmaceutically acceptable salt (inorganic or organic) or complex. It may be in an optically pure form or a mixture of stereoisomers.

DETAILED DESCRIPTION

An important aspect of the benefits of "TRNA" or "RNA" BONATH" therapy in CNS drug delivery for brainstem related disorders lies in the anatomy of the region. The free nerve endings with receptors for the neuro-chemicals dopamine, serotonin, norepinephrine, and others are located just below the surface of the skin, easily assessable to drugs compounded in an appropriate dermal penetration enhancing medium and topically applied to the skin.

An important component of the brainstem autonomic nervous system is the "flight or fight" (sympathetic) response responsible for protecting an individual from danger. Programmed to act "automatically" without time-consuming thought, it results in physiological and emotional manifestations reflective of either fleeing from or fighting/confronting perceived danger. Often, the difference between the two is not clearly delineated, as in most situations, the response is mixed.

Norepinephrine (noradrenaline) and serotonin are considered the principal neurotransmitters involved with the sympathetic autonomic system "fight or flight" response. Dopamine and acetylcholine (primarily affects the parasympathetic system) also play roles. The collections of neuronal nuclei responsible for the production of these neurotransmitters reside in the brainstem. The locus ceruleous contains neurons which produce norepinephrine, the dorsal raphe is responsible for serotonin production, and the substantia nigra, for dopamine. Acetylcholine is produced in a more widespread fashion.

It is now widely accepted that mood disorders are related to dysregulation of neurotransmitters—"brain chemical imbalance". Drug therapies are directed at "re-establishing neurochemical balance" in the brain through the use of serotonin re-uptake inhibitors (SSRI's) and serotonin and norepinephrine re-uptake inhibitors (SNRI's). Although these drugs are effective, they take several weeks to months to show significant benefit. Furthermore, their clinical effect is most pronounced for the chronic symptoms related to depression and anxiety. They are ineffective or less effective than desired for the episodic acute symptoms of anxiety reactions and panic attacks which commonly accompany these chronic conditions. To this end, acute treatment for break-through episodes has been in the form of oral or injectable anxiolytics, depending on severity of symptoms. Commonly used drugs are the benzodiazepines: lorazepam (Ativan), diazepam (Valium), clonazepam (Klonopin), chlordiazepoxide (Librium), and alprazolam (Xanax). For particularly severe symptoms, neuroleptics and psychotropics may also be used: chlorpromazine (Thorazine), haloperidol (Haldol), risperidone (Risperdal), olanzapine (Zyprexa) and quetiapine (Seroquel).

Oral and injectable anxiolytics and neuroleptics/psychtropics must rely on systemic blood (and therefore, blood levels) for eventual effect on the brain. This is associated with undesirable systemic side-effects, particularly fatigue and lethargy acutely post-dose. With chronic use, psychological dependency, tardive dyskinesia, Parkinsonism, obesity, and insulin resistance may be encountered. With oral preparations, there is delay (½ to several hours) before significant clinical effect. In some situations, this degree of delay is unacceptable as profound clinical decompensation may result. An example is a panic attack in a predisposed individual that leads to a psychotic breakdown or a non-epileptic/psychogenic seizure. The clinical consequence for such an affected individual is significant. There is also the additional financial expense of an emergency room visit or hospitalization.

Mood changes with symptoms of anxiousness, sadness, and elation are part of the human experience. These normal emotions of life become problematic when they become severe, persistent, and interfere with functional ability. It is at this point that medical intervention needs to be considered. Whether one gets to the point of requiring medical therapy is dependent on several factors. One is the innate nature of the person's make-up: how they are "wired and programmed" to deal with the issues of life. Some of this relates to family history, growth and development pre and post-natally (intra-uterine insult and birth trauma), and one's basic emotional and philosophical outlook. The external factors consist of stressors impinging on the individual: relational, physical (illness and disability), financial, work-related, etc. In this regard, it is not just the degree of stress that is important but also the length of time associated. Certain life events are universally stressful for all individuals: death of a loved one, divorce, losing a job. Still, how these events specifically impact an individual depends on one's coping mechanisms and the specifics of the event for that individual.

Psychologists have devised a "life crisis unit" scale (LCU's) for emotionally significant life stress events. The scale ranges from 0 to 100, with the more emotionally significant events in the higher range. It has been determined that if an individual accumulates 250-300 points over a relatively short period, 3-4 months, they are at risk for a nervous breakdown and/or significant physical illness. Accordingly, individuals at risk from innate make-up are particularly prone to decompensation when such-external stress events come in to their lives. These are the people who experience frequent panic attacks and emotional breakdowns. Their lives are significantly disrupted and they may become emotionally disabled.

These individuals require prompt recognition with the institution of early, appropriate therapy. Untreated, they are prone to the phenomenon of pervasive dysfunction from persistent neuronal hyper-excitability/dysfunction. This, in turn may result in re-programming of neural circuits with accompanying permanent psychological and behavioral changes. This progression of events is akin to the process of "kindling" which occurs in epileptic conditions: untreated or inadequately treated seizure foci spread to other areas of the brain and become increasingly resistant to therapy. The new foci of neuronal hyper-excitability may be adjacent to the original or cross over the corpus callosum as a "mirror focus".

A similar phenomenon occurs in migraine, a condition with increased propensity to neuronal hyper-excitability in the brainstem with peripheral and cortical sensitivity to triggers. If treatment is rendered late or inadequately, there is a greater likelihood for more severe and persistent symptoms. In this regard, young migraneurs also need to be identified early and treated to reduce life-long disability from chronic, severe migraines.

The "fight or flight" sympathetic system response, interpreted as stress, is in the most basic sense, a fear-based reaction: fear of the uncertainty related to significant life stress events. The experienced fear may be real or perceived but the effect is the same: perceived danger as the individual's sense of control and stability is threatened. Interestingly, as the LCU scale suggests, the more emotionally significant the event, the more likely it results in a stress reaction. Even "positive" stress (job promotion with increased responsibilities) may have negative effects similar to the negative event of being fired from a job. In this respect, "stress" may be defined as: any change that significantly alters one's status quo and questions the individual's sense of security and stability physically, emotionally, or relationally.

As the sympathetic nervous system serves to protect the individual, it is easy to understand that it is also intimately involved with pain perception in addition to the psychological response. In fact, the two systems go hand-in-hand: the more severe the perceived pain, the greater the emotional toll and likelihood for depression; and vice-versa, a depressed individual perceives pain more acutely than one who is not. It is also recognized that "emotional" pain (heartbreak) disrupts brainstem function and more significantly affects the individual than physical pain such as that associated with a heart attack or a broken arm. The emotions of fear, betrayal, and abandonment may be attached to the former. The neurotransmitters norepinephrine and serotonin have both been recognized to play significant roles in the human psychological and pain response. Drugs which modulate, increase, and balance the levels of these two brain chemicals have been approved for both mood and pain syndromes.

The SNRI's duloxitine (Cymbalta®) and venlafaxine (Effexor®), as well as the older tricyclic antidepressants, such as amytriptilene (Elavil®), have shown benefit for depression and for neuropathic pain, with or without associated mood dysfunction.

There have also recently come on the scene, drugs in the category of "neuro-modulators" which treat neurochemical imbalance and dysfunction syndromes indirectly. Gabapentin (Neurontin®) and pregabalin (Lyrica®) are specific calcium channel modulators which influence serotonin and norepinephrine release at their repective receptors. They are indicated for such diverse and seemingly different conditions as: focal onset seizures, post-herpetic neuralgia, diabetic peripheral neuropathy, fibromyalgia, anxiety, and drug withdrawl syndromes. The commonality in these conditions is that there has occurred some component of neurologic injury with resultant persistent neuronal hyper-excitability and dysfunction. The abnormally increased activity of these neuronal populations in turn results in neurochemical imbalance. These neuro-modulating drugs act to suppress such activity and re-establish neurotransmitter equilibrium. The resultant specific symptom reduction or resolution depends on the specific location and functions of the affected neuronal population.

Many anti-epileptic drugs have also been found of benefit in psychological conditions manifesting significant fluctuations and swings in mood. Bipolar affective disorder (manic-depressive disorder) is such a disorder, alluding there is likely neuronal hyper-excitability involved with these conditions. Thus, it is the specific population of neurons and their connections which determine the symptoms experienced by the patient. The seizure drugs valproic acid (Depakote®) and lamotrigene (Lamictal®) are both indicated for bipolar affective disorder in addition to their initial indications for epilepsy. Anti-epileptic drugs, together with anti-depressants and anxiolytics are used in the treatment of "non-epileptic"/psychogenic seizures, an involuntary, conversion reaction disorder with significant psychological disability. The anti-epileptics Depakote and Topamax are also FDA approved for migraine headache prophylaxis, suggesting the association of hyper-excitable neuronal populations requiring stabilization with this condition.

Approved medical therapy for Parkinson's disease (PD) in the United States is limited to oral and subcutaneous (sub-Q) injection. The tablet, in ordinary or oral-dissolving form (ODT), is used to deliver levodopa to the central nervous system (CNS) in combination with carbidopa (Sinemet®) or with a COMT inhibitor (Comtan®); dopamine agonists, MAO inhibitors, COMT inhibitors, and other agents also use the oral route. Apomorphine, as sub-Q injection (Apokyn®), is approved for the acute treatment of episodes of hypomobility/off-periods associated with PD. In Europe, apomorphine is also given by intra-peritoneal pump. All current treatment modalities are considered "systemic" in that ultimate therapeutic effect relies on blood flow: first the general circulation, then, the cerebral blood, to reach target sites in CNS. This also holds true for the transdermal dopamine agonist (rotigotine) patch, Neupro®, which, applied to the skin, required absorption into sub-Q vessels for eventual delivery to CNS. Neupro was removed from the U.S. market after technical problems with crystallization within the patch matrix but remains available in Europe. Studies are underway to reintroduce it in the U.S.

The widespread presence of active drug in systemic and cerebral blood is likely the primary source of side-effects associated with PD drugs. As stimulation of dopamine receptors and other neuro-chemical effects occur at regions other than those targeted, unwanted drug effects occur. Further, with reliance on blood flow for therapeutic effect, idiosyncrasies in the cardiovascular and cerebrovascular systems need to be considered. Heart disease and atherosclerosis, both common in elderly PD patients, can significantly affect systemic drug delivery. With oral delivery of PD medications, gastrointestinal (GI), disease affecting GI transit, absorption, and hepatic metabolism are concerns.

Systemic delivery of PD drugs also raises the concern of "non-physiologic effects" as active drug is delivered to "downstream" neuro-anatomical structures in advance of those "upstream." Within the dopaminergic system, normal physiological sequence of neuro-chemical flow and effect is from brainstem (substantia nigra) to striatum (caudate and putamen) by ascending nigra-striatal pathways. Accordingly, therapeutic effect would seem best realized when PD drug effect follows the same neuro-physiological sequence. This may particularly hold true for dopamine precursors and agonists. The long term dopamine therapy effects of "receptor hypersensitivity," manifest as motor complications and "on-off phenomena," may be the consequence of persistent, fluctuating, non-physiologic "downstream" dopamine receptor stimulation.

All currently approved therapies for the conditions described above reach the central nervous system through the systemic circulation. Cerebral blood flow to brainstem structures is through the posterior circulation, via the vertebral and basilar arteries and their branches. In view of the undesirable side-effects associated with this form of drug delivery to the brain, the present invention is directed in part to the targeted regional delivery to the brainstem.

To understand the concept of "peripheral de-afferentation" as it applies to the brainstem and how topical drug delivery to the back of the neck works requires a review of the neuro-anatomy and the neuro-physiology of the region. As indicated above, this area of the nervous system is very complicated, compact and highly inter-active and inter-related.

The Trigeminal Nerve System is a component of the brainstem which coordinates pain input from the face, head, and the back of the neck. As such, it intimately influences the production of other symptoms associated with syndromes attributed to dysfunction within the trigeminal complex. These include the photophobia, phonophobia, nausea, anxiety, allodynia, and other focal sensory symptoms which may accompany a migraine attack. Similarly, episodes of trigeminal neuralgia (tic douloreux) frequently involve significant affective (emotional) and visceral components. Because of proximity and connections to other structures in the brainstem, abnormalities of temperature regulation, thirst, alertness, and mood are common. Some of these symptoms may be as equally disabling as the head and face pain.

In addition to receiving pain and sensory (afferent) input from the face, nasal and para-nasal sinuses, the teeth, scalp, the dura of the anterior and middle cranial fossa, the trigeminal system receives similar input from the soft tissues of the posterior cervical region. The free nerve endings in the back of the neck are just below the surface of the skin, easily accessible to topically delivered drugs formulated in an appropriate dermal penetration enhancing compounding medium. The free nerve endings, via the small un-myelinated and myelinated "C-fibers" (pain fibers) carry pain impulses through afferent sensory nerves back to the Trigeminal Nucleus Caudalis (TNC). TNC is the pain processing center extending from the pons through the entire extent of the brainstem to the upper cervical spinal cord. After synapsing at the thalamus, pain impulses from TNC travel to the somatosensory cortex, where pain is perceived.

As providing important afferent input to the brain, the trigeminal system also receives afferent input from the rest of the body. Affarent input is defined as any neural impulses coming back to the brain from the body. As such it provides information to the brain for processing and interpretation: pain, sensation, autonomic functions. Efferent output, on the other hand, consists of impulses originating in the central nervous system (brain, brainstem, and spinal cord) flowing to the body for function: movement, response, action.

The vagus nerve includes both efferent and afferent fibers and is attached to the lower brainstem (medulla oblongata) via 8-10 radicles. The afferent fibers arise in the jugular and the nodose vagus ganglia. The somatic afferent fibers terminate in the nucleus of the trigemino-spinal tract (TNC). Both the jugular and the nodose ganglia are connected with the superior cervical sympathetic gangion through inter-communicating rami. The superior cervical sympathetic ganglion is located between the internal carotid artery and the jugular vein on the ventral aspects of the transverse processes of the 2nd, 3rd, and the 4th cervical vertebrae. It is the largest of the sympathetic trunk ganglia.

Sympathetic roots arising from the ganglion join the 1st and the 2nd cervical nerves; frequently the 3rd, and occasionally, the 4th. In addition to nerve fibers which extend rostrally from the superior cervical sympathetic ganglion, the sympathetic innervation of the head includes fibers which join the plexi on the common carotid and the vertebrtal arteries. The one on the vertebral artery is continuous with the plexus on the basilar artery. Rami derived from the internal carotid plexus join the trigeminal nerve and the cavernous plexus in addition to the other structures such as the abducens and deep petrosal nerves. From the cavernous plexus, located in the middle cranial fossa, sympathetic fibers join the oculomotor, trochlear, and the ophthalmic nerves. Fibers from the plexus also accompany blood vessels into the hypophysis.

The spheno-palatine gangion, located in the pterygo-palatine fossa, receives sypmpathetic fibers from the face with rami distributed to the mucous membranes of the nares, mouth, the pharynx, and some orbital structures.

From the above, it is clear that cervical nerve function is intimately related to vagal afferents and afferents from the face, head, and the dura of cranial fossae associated with migraine and other head and face pain syndromes.

It has been long reported that vagal nerve stimulation (VNS) in the neck down-regulates abnormal discharges from epileptic foci and treats seizures. VNS is now approved as adjunct to medical therapy in certain forms of intractable epilepsy. It is also of benefit in severe depression resistant to traditional drug therapy. Studies with VNS in migraine, anxiety, and fibromyalgia have been underway and have shown preliminary promise in benefit.

The mechanism of action appears to be the down-regulation of hyper-excitable, dysfunctional neuronal systems by increased inhibitory input to brainstem and associated connections through stimulation of the afferent system. Affarent stimulation, by feed-back through TNC, causes reduction in efferent output from the brainstem, resulting in resolution of clinical symptoms through down-regulation of hyper-active neuronal structures.

In the same way the electrical stimulation of VNS accomplishes its effect on the brainstem, topical drug therapy to the posterior cervical region, in close proximity to the brainstem and its afferent inputs, is theorized to provide effect for the conditions mentioned above. Thus, drugs proved of benefit for these disorders, show improved efficacy with diminished side-effects if delivered in the manner suggested. Other drugs being developed for these conditions should similarly be considered for such delivery.

It is hypothesized that benefits of the present method of topical drug delivery of central nervous system (CNS) active drugs lies in the fact that drug concentration gradients and blood flow factors are un-involved in the therapeutic process. In contrast, the proposed delivery operates through direct nerve connections between skin peripheral nerves at the back of the neck at the hairline (BONATH) and brainstem structures. Active drug compounded in an appropriate "dermal penetration enhancing" medium topically applied to the skin at the back of neck has effect on the free nerve endings of peripheral nerves located immediately below the skin surface. Receptors to dopamine, serotonin, norepinephrine, and other neuro-transmitters/neuro-chemicals involved with neural transmission are located on these free nerve endings. Therefore, topically applied drug has near immediate therapeutic effect as direct neural impulses are involved—the concept of brainstem afferent stimulation through topical regional neuro-affective (TRNA) therapy. All prior art and methods of drug delivery to the CNS have involved blood flow and therapeutic drug blood level requirements. The proposed method does not require such, which are the source of undesirable systemic and CNS side-effects. The presently proposed drug delivery process operates on the principle of an electrical capacitor whereas the prior relied on those fluid dynamics and reservoir principles.

The factors which determine the success of TRNA therapy include: the drug being considered, the compounding substance (surfactant/dermal penetration enhancer), the disease process, and the location of application. For migraine, face and head pain syndromes, Parkinson's disease, and other conditions relying on afferent input to or through the cervical cord and brainstem, it is believed that the currently proposed method is ideal. The free nerve endings in the skin at the back of the neck are important components of the cervical nerves with rich connections to the trigeminal, vagal, and sympathetic systems communicating with brainstem structures and other components of the central nervous system. These are the areas pain and other symptoms related to neuro-chemical release are processed and perceived.

The skin at the upper part of the back of the neck, at the hairline, is innervated by (supplied by nerves) the cervical nerve roots C1-3 that are also part of the Trigeminal Nerve system of the brainstem. These cervical nerves (the wires) have their cell bodies (their generators) within the Nucleus Caudalis (Spinal Nucleus) of the Trigeminal Nerve in the cervical spinal cord and the brainstem. Accordingly, they have direct neural connections with brainstem processing areas. At the same time, the peripheral nerve receptor sites for these nerves, the free nerve endings, reside under the skin surface at the back of the neck. The nerves in the soft tissues of the back of the neck, representing the C1, C2, and C3 segments of the cervical spinal cord are unique in that they have intimate connections with pathways directly affecting brainstem and autonomic system function. There are direct connections with the Trigeminal Nerve system of the brainstem which provides for pain and other sensory input and interpretation from the head, face, sinus cavities, the dural covering of the brain, and the back of the neck. There are also connections with the vagus nerve and the sympathetic nervous system through the sympathetic ganglia. Thus, it is through these connections, which are nowhere else in the body as inter-related or at such close proximity to the surface of the human skin, that the potential for the delivery of CNS acting drugs through the skin at the back of the neck (BONATH) is realized. Finally, skin is embryologically derived from neuro-ectoderm which is also responsible for the formation of the brain and other aspects of the CNS. Thus, the nerves in the human skin have a particularly direct relationship with these structures. This provides for the efficacy noted with TRN BONATH therapy. At the same time, systemic and other CNS side-effects are reduced or avoided. Thus, drugs topically applied to the skin in this region have ready access to brainstem and other CNS structures without the requirement of drug in the bloodstream reaching target sites.

In addition to the upper cervical nerves having direct relation to the Trigeminal Nerve System, they also contribute to the Cervical Sympathetic Ganglia and the Vagal Nerve Systems through direct connections. These latter two systems provide some of the most significant afferent feed-back to the brainstem and other portions of the CNS from the rest of the body. This allows for additional brainstem afferent stimulation potential through TRNA therapy at the back of the neck. Although skin at other areas of the face and head have eventual neural feed-back to the brainstem, the intimate connections to afferent feed-back systems are lacking.

To understand the concept of peripheral afferent stimulation (or "de-afferentation") as it applies to brainstem afferent stimulation and how topical drug delivery to the back of the neck works requires a review of the neuro-anatomy and the neuro-physiology of the region. As indicated above, this area of the nervous system is very complicated, compact and highly inter-active and inter-related.

The Trigeminal Nerve System is a component of the brainstem which coordinates pain input from the face, head, and the back of the neck. As such, it intimately influences the production of other symptoms associated with syndromes attributed to dysfunction within the trigeminal complex. These include the photophobia, phonophobia, nausea, anxiety, allodynia, and other focal sensory symptoms which may accompany a migraine attack. Similarly, episodes of trigeminal neuralgia (tic douloreux) frequently involve significant affective (emotional) and visceral components. Because of proximity and connections to other structures in the brainstem, abnormalities of temperature regulation, thirst, alertness, and mood are common. Some of these symptoms may be as equally disabling as the head and face pain.

In addition to receiving pain and sensory (afferent) input from the face, nasal and para-nasal sinuses, the teeth, scalp, the dura of the anterior and middle cranial fossa, the trigeminal system receives similar input from the soft tissues of the posterior cervical region. The free nerve endings in the back of the neck are just below the surface of the skin, easily accessible to topically delivered drugs formulated in an appropriate dermal penetration enhancing compounding medium. The free nerve endings, via the small un-myelinated and myelinated "C-fibers" (pain fibers) carry pain impulses through afferent sensory nerves back to the Trigeminal Nucleus Caudalis (TNC). TNC is the pain processing center extending from the pons through the entire extent of the brainstem to the upper cervical spinal cord. After synapsing at the thalamus, pain impulses from TNC travel to the somatosensory cortex, where pain is perceived.

As providing important afferent input to the brain, the trigeminal system also receives afferent input from the rest of the body. Afferent input is defined as neural impulses coming back to the brain from the body. As such, it provides information to the brain for processing and interpretation: of pain, sensation and other perception, motor, and autonomic functions. Efferent output, on the other hand, consists of impulses originating in the central nervous system (brain, brainstem, and spinal cord) flowing to the body for function: movement, response, action.

The nerves in the soft tissues of the back of the neck, representing the C1, C2, and C3 segments of the cervical spinal cord are unique in that they have intimate connections with pathways directly affecting brainstem and autonomic system function. The brainstem represents the primary neural relay and processing center of the body. In the human, it is the size of the thumb and contains the most dense and complicated network of neural connections any where. It functions to relay all neural impulses from the brain to the body (efferent output) as well as receive them back from the body to the CNS for processing (afferent input).

There are direct connections between the nerves in the skin at the back of the neck and the Trigeminal Nerve system of the brainstem, which provides pain and sensory input and processing from the head, face, sinus cavities, and the dural covering of the brain. There also exist afferent connections with the vagus nerve and the sympathetic nervous system through the sympathetic ganglia. It is through these connections, which are nowhere else in the body as inter-related or at such close proximity to the surface of the human skin as at the back of the upper neck (BONATH), that the potential for the delivery of CNS active drugs through TRNA therapy is realized. As providing important afferent input to the brain, the trigeminal system also receives afferents from the rest of the body.

The vagus nerve includes both efferent and afferent fibers and is attached to the lower brainstem (medulla oblongata) via 8-10 radicles. The afferent fibers arise in the jugular and the nodose vagus ganglia. The somatic afferent fibers terminate in the nucleus of the trigemino-spinal tract (TNC). Both the jugular and the nodose ganglia are connected with the superior cervical sympathetic gangion through inter-communicating rami. The superior cervical sympathetic ganglion is located between the internal carotid artery and the jugular vein on the ventral aspects of the transverse processes of the $2^{nd}$, $3^{rd}$, and the $4^{th}$ cervical vertebrae. It is the largest of the sympathetic trunk ganglia.

Sympathetic roots arising from the ganglion join the $1^{st}$ and the $2^{nd}$ cervical nerves; frequently the $3^{rd}$, and occasionally, the $4^{th}$. In addition to nerve fibers which extend rostrally from the superior cervical sympathetic ganglion, the sympathetic innervation of the head includes fibers which join the plexi on the common carotid and the vertebrtal arteries. The one on the vertebral artery is continuous with the plexus on the basilar artery. Rami derived from the internal carotid plexus join the trigeminal nerve and the cavernous plexus in addition to the other structures such as the abducens and deep petrosal nerves. From the cavernous plexus, located in the middle cranial fossa, sympathetic fibers join the oculomotor, trochlear, and the ophthalmic nerves. Fibers from the plexus also accompany blood vessels into the hypophysis (pituitary gland). The spheno-palatine gangion, located in the pterygopalatine fossa, receives sympathetic fibers from the face with rami distributed to the mucous membranes of the nares, mouth, the pharynx, and some orbital structures.

From the above, it is clear that upper cervical (C1-4) nerve function with peripheral nerve free nerve endings in the skin at the back of the neck (BONATH) is intimately related to vagus nerve afferents and afferents from the face, head, and the dura of cranial fossae through the trigeminal nerve. These, in turn, provide feedback to the brainstem and other CNS structures for nerve signal processing.

It has been long reported that vagal nerve stimulation (VNS) in the neck down-regulates abnormal discharges from epileptic foci and treats seizures. VNS is now approved as adjunct to medical therapy in certain forms of intractable epilepsy. It is also of benefit in severe depression resistant to traditional drug therapy. Studies with VNS in migraine, anxiety, and fibromyalgia have been underway and have shown preliminary promise in benefit.

The mechanism of action appears to be the down-regulation of hyper-excitable, dysfunctional neuronal systems by increased inhibitory input to brainstem and associated connections through stimulation of the afferent system. Afferent stimulation, by feed-back through TNC, causes reduction in efferent output from the brainstem, resulting in resolution of clinical symptoms through down-regulation of hyper-active neuronal structures.

In the same way the electrical stimulation of VNS accomplishes its effect on the brainstem, topical drug therapy to the posterior cervical region, in close proximity to the brainstem and its afferent inputs, is theorized to provide effect for the conditions mentioned above. Thus, drugs proved of benefit for these disorders, show improved efficacy with diminished side-effects if delivered in the manner suggested. Other drugs being developed for these conditions should similarly be considered for such delivery.

The question arises then: does TRNA therapy work with drug application to the forehead, face, or other regions of the head. The answer is perhaps—in some disease states such as migraine and face pain; but, not as effective and efficient as at the back of the neck at the hairline, BONATH. Free nerve endings are also present at these other locations but the distance back to involved brainstem structures is greater and there is not the added advantage of rich afferent neural connections to the trigeminal, vagal, and sympathetic nerve systems which are associated with the posterior cervical region.

"TRNA BONATH" delivery differs from traditional therapy (whether oral, injection, nasal spray, inhalation, or rectal) in that it has no reliance on the systemic or cerebral blood flow. Nor does it require therapeutic blood levels of drug. These latter factors are responsible for systemic and CNS side-effects as drug is delivered to areas not intended to be affected in the therapeutic process. Transdermal systemic delivery by patch, although similarly applied to the skin as in TRNA BONATH therapy, differs significantly in its reliance on a drug concentration gradient for absorption into the systemic capillary and venous blood. TRNA therapy is unaffected by dermal vessels or systemic blood flow. It relies solely on the function of the free nerve endings of cutaneous nerves and their connections at the point of application of compounded drug.

"Traditional" transdermal drug delivery by patch and TRNA are both "transdermal" in that in bath, drug penetrates the skin (epidermis) for eventual clinical effect. The difference lies in the fact that in "traditional" transdermal patch therapy, drug enters the systemic circulation through a concentration gradient and establishes a therapeutic drug blood level. Although measuring a blood level gives assurance drug is being taken or delivered systemically, allowing for checking compliance, it is also the source of undesirable side-effects and drug interactions. Of necessity, with systemic transdermal patch therapy, drug applied to the skin surface must be absorbed through the small vessels in the dermis for eventual presence in the systemic venous blood for measurement of drug level. With the proposed TRNA therapy, drug need only be available at the free nerve endings under the epidermis. No concentration gradients or systemic blood levels are necessary. Drug delivery is unaffected by cardiac output or cerebral blood flow factors. Of significance, persons afflicted with Parkinson's disease are typically elderly with concomitant cardiac and cerebral vascular disease.

Thus, in certain embodiments, the methods and formulations of the invention deliver an amount of drug (e.g., dopamine agonist) in the TRNA therapy that would provide sub-therapeutic plasma levels if administered orally, but which is therapeutically effective when administered via TRNA therapy at the BONATH.

It is hypothesized by the inventor that a principal reason TRNA therapy is rapid in the onset of clinical effect (e.g., less than about 10 minutes for migraine with topical sumatriptan and less than about 15 minutes for Parkinson's disease with topical apomorphine) is that it operates through an "electrochemical" process. Active drug compounded in an appropriate dermal penetration enhancing medium acts at free nerve endings, changing the neurochemistry of receptors at the neural synapse: apomorphine (dopamine and norepinephrine agonist), increasing dopamine and norepinephrine levels and improving neural transmission. After a point of receptor stimulation, neural (electrical) impulses are generated back to neuronal cell bodies residing in the spinal cord and brainstem: "afferent feed-back". The nervous system functions through neurons generating electrical impulses and the release of neurochemicals/neuro-transmitters (serotonin, norepinephrine, dopamine, and acetylcholine, being the major ones) at neural receptor sites called "synaptic clefts". Accordingly, the process in TRNA therapy may be considered analogous to an electrical capacitor discharging to perform a function, such as turning on a light switch. Viewed from this perspective, the rapid onset of clinical effect observed in TRNA therapy makes sense.

It is further hypothesized that via the use of TRNA therapy, the dopamine stimulation of receptors in the Nigra-striatal System is physiological and down-stream: from the cutaneous free nerve-endings to the cervical cord, to the brainstem and substantia nigra; then, via ascending nigra-striatal connections to the dopamine receptors within the caudate and putamen. With systemic (oral, injection, or patch) the downstream anatomical regions (caudate and putamen) may be stimulated in advance of or at the same time as the upstream (brainstem) components. The inventor believes that much of the chronic motor complications of dopamine therapy are the result of this phenomenon—the result of "dopamine receptor hypersensitivity". This complication is believed to be avoided, and in fact, alleviated through TRNA dopamine delivery, in which it is believed that the dopamine and other neurochemical effects are physiological and flow in the direction and manner in which they were intended—and therefore, most effective.

Alternatively, transdermal systemic patch delivery operates on the principles of chemical gradients and fluid dynamics. These processes have variability and inherent idiosyncrasies, fluctuating heart function as a pump for blood flow being one. Thus, despite the advantage of measurable drug levels, a more circuitous route with slower clinical effect is observed. This makes systemic transdermal patch delivery inappropriate for acute therapy.

Alternatively, rapid as well as prolonged clinical effect may be achieved by a sustained-release dermal system employing the principles of TRNA therapy through patch application at the skin at the back of the neck at the hairline (BONATH). BONATH refers to the specific site of topical drug application necessary for clinical effect in TRNA therapy. The location is critical in TRNA therapy, whereas, with the transdermal systemic patch, location is irrelevant. The uniqueness of this particular area of the human anatomy which allows this delivery method to work is discussed below.

Alternatively, TSD therapy, the traditional transdermal systemic delivery, operates on the principles of chemical gradients and fluid dynamics. These processes have associated inherent idiosyncrasies and variabilities; heart function as a pump for blood flow being one. Accordingly, despite the advantage of measurable drug levels, traditional transdermal systemic delivery involves a more circuitous route with slower clinical effect.

Rapid as well as prolonged clinical effect may be achieved by a sustained-release patch placed at the same anatomical site, BONATH.

One skilled in the art having the benefit of the information contained herein will appreciate that there are many classes of drugs which would be useful for topical brainstem de-afferentation therepy. These classes of drugs include, but are not limited to:

1. Anti-Epileptic drugs: Examples include Valproic acid (Depacon®/Depakot®e), Leviteracetem (Keppra®), Lamotrigene (Lamictal®), Topiramate (Topama®x), Pregabalin (Lyrica®), Gabapentin (Neurontin®), Carbamazepine (Tegretol®), Oxcarbazepine (Trileptal®), Phenobarbital and other barbiturates, Tiagabine (Gabatril®), Retigabine™ (Valeant Pharmaceuticals), Lacosamide® (Schwarz Biosciences), and Perampanel® (Eisai) are in development as anti-epileptics and neuromodulators for other associated neurological, pain, and psychiatric conditions.
2. Anxiolytic drugs: Benzodiazepines: Examples include lorazepam (Ativan®), diazepam (Valium®), clonazepam (Klonopin®), chlordiazepoxide (Librium®), and alprazolam (Xanax®).
3. Neuroleptics/Anti-Psychotic drugs: Examples include chlorpromazine (Thorazine®), haloperidol (Haldol®), risperidone (Risperdal®), olanzapine (Zyprexa®) and quetiapine (Seroquel®).
4. Analgesics/Anti-Inflammatory drugs: Examples include prednisone, solumedrol, and other steroids, naproxen, aspirin, acetaminophen, voltaren, ketoprofen, ibuprofen, other NSAID's.
5. Parkinson's Disease/Similar or Related Syndrome drugs: Examples include dopamine agonists such as apomorphine.
6. Sexual Dysfunction drugs: Examples include dopamine agonists such as apomorphine.
7. Dystonia (cervical and otherwise), which sometimes occur in conjunction with spasmodic torticollis and spastic conditions: Examples of drugs include dopamine agonists such as apomorphine.
8. Benign essential/familial tremor, tremor related to MS, chronic encepahalopathies such as from stroke or head injuries, congenital CNS degeneration conditions/cerebral palsy, cerebellar degeneration syndromes, and spasicity conditions from the above: Examples of drugs include dopamine agonists such as apomorphine.
9. Neuropathic/Neurogenic pain drugs: Examples include carbamazepine, gabapentin, topiramate, zonisamide, phenytoin, desipramine, amitriptyline, imipramine, doxepin, protriptyline, pentoxifylline, and hydroxyzine.
10. Smoking Cessation drugs: Examples include drugs such as varenicline.
11. Appetite Suppressant drugs: Examples include drugs such as Sibutramine.
12. Neurodegenerative Diseases: Examples include drugs such as Aricept/donepezil, Exelon/rivastigmine, Reminyl/

Razadyne/galantamine, and Namenda/memantine and their naturally occurring counterparts, as well as NMDA antagonists.

13. Multiple Sclerosis (MS): Examples include drugs such as 4-aminopyridine.
14. Insomnia: Examples include drugs such as zolpidem.
15. Fatigue: Examples include drugs such as pemoline and Modafinil.
16. Vertigo, Nausea and/or Dizziness: Examples include drugs such as as meclizine, dimenhydrinate, prochlorperazine, scopolamine and diphenhydramine.
17. Writer's cramp and restless leg syndrome: Examples include dopamine agonists such as apomorphine.
18. ADD/ADHD: Examples include drugs such as lisdexamfetamine, methylphenidate.

In general, the formulations and methods described herein are useful for the treatment of neuronal hyperexcitability and neurochemical dysfunction syndromes and the drug may be, e.g., an anti-epileptic, an anxiolytic, a neuroleptic, an antipsychotic, an analgesic, an anti-inflammatory, an anti-Parkinson's disease/syndrome drug, a sexual dysfunction drug, a drug for the treatment of dystonia, a drug for the treatment of spastic conditions, a drug for the treatment of benign essential/familial tremor, a drug for the treatment of tremor related to MS, a drug for the treatment of chronic encepahalopathies, a drug for the treatment of congenital CNS degeneration conditions/cerebral palsy, a drug for the treatment of cerebellar degeneration syndromes, a drug for the treatment of neuropathic and/or neurogenic pain, a drug for smoking cessation, a drug for appetite suppression, a drug for neurodegenerative conditions, a drug for the treatment of multiple sclerosis, a drug for the treatment of insomnia, a drug for the treatment of fatigue, a drug for the treatment of vertigo, nausea and/or dizziness, a drug for the treatment of writer's cramp and restless leg syndrome, a drug for the treatment of ADD/ADHD, and other drugs which can beneficially be administered at the the back of the neck at the hairline in close proximity to and under or on the area of skin above the brain stem to provide regional neuro-affective therapy to the patient.

In certain embodiments, the drug is a dopamine agonist such as apomorphine (Apokyn®, APO-go®), pramipexole (Mirapexin®), ropinirole (Requip®), bromocriptine (Parlodel®), cabergoline (Cabaser®, Dostinex®), pergolide (Permax®, Celance®) rotigotine (Neupro®), mixtures of any of the foregoing, or other dopamine agonists known to those skilled in the art. One skilled in the art will appreciate that dopamine agonists other than apomorphine may be used in the formulations and methods of the present invention, and all such agents are meant to be encompassed by the term "dopamine agonists." For example, such drugs include, but are not limited to, carbidopa (Sinemet®), dopamine agonists (Requip®, Rotigotine®, Mirapex®), COMT inhibitors (Entacapone®, Tocapone), rasagiline (Azilect®) (MAO inhibitors) and MAO-B inhibitors (Selegiline (Eldepryl®).

In other embodiments, the drug is opioid such as morphine, codeine, dihydrocodeine, hydrocodone, hydromorphone, nicomorphine, oxycodone, oxymorphone, fentanyl, alphamethylfentanyl, alfentanil, sufentanil, remifentanil, carfentanyl, ohmefentanyl, thebaine, oripavine, diacetylmorphine (heroin), phenylpiperidines such as pethidine (meperidine) and ketobemidone, allylprodine, prodine, propoxyphene, dextropropoxyphene, dextromoramide, bezitramide, piritramide, methadone, dipipanone, levomethadyl Acetate (LAAM), loperamide, diphenoxylate, dezocine, pentazocine, phenazocine, buprenorphine, dihydroetorphine, etorphine, butorphanol, nalbuphine, levorphanol, levomethorphan, lefetamine, meptazinol, tilidine, tramadol, tapentadol, mixtures thereof, and the like.

In yet other embodiments, the drug is tarpentadol (a centrally acting oral analgesic having two mechanisms of action combining mu-opioid receptor agonism and norepinephrine reuptake inhibition).

In yet other embodiments, the drug is a selective norepinephrine reuptake inhibitor, such as Atomoxetine (Strattera®), Mazindol (Mazanor®, Sanorex®), Nisoxetine (LY-94939), Reboxetine (Edronax®, Vestra®), Viloxazine (Vivatan®), mixtures thereof, and the like.

In yet other embodiments, the drug is a benzodiazepine, such as lorazepam (Ativan®), diazepam (Valium®), clonazepam (Klonopin®), chlordiazepoxide (Librium®), alprazolam (Xanax®), temazepam (Restoril®), mixtures thereof, and the like. In other embodiments, the drug is a neuroleptic or psychotropic such as chlorpromazine (Thorazine®), haloperidol (Haldol®), risperidone (Risperdal®), olanzapine (Zyprexa®) and quetiapine (Seroque®).

In other embodiments, the drug is an agent that treats depression and/or anxiety, for example, selective serotonin reuptake inhibitors (SSRIs) such as fluoxetine (Prozac), sertraline (Zoloft®), venlafaxine (Effexor®), citalopram (Celexa®), parocetine (Paxil), mixtures thereof, and the like (such as trazodone (Desyrel)), and/or serotonin-norepinephrine reuptake inhibitors (SNRI), such as Desvenlafaxine (Pristiq®), Duloxetine (Cymbalta®), Milnacipran (Ixel®, Savella®), Venlafaxine (Effexor®), mixtures thereof, and the like.

In yet other embodiments, the drug is a norepinephrine-dopamine reuptake inhibitor (NDRI), such as Amineptine (Survector®), an aminoketone antidepressant such as Bupropion (Wellbutrin®, Zyban®), Dexmethylphenidate (Focalin), Methylphenidate (Ritalin®, Concerta®), Nomifensine (Mental®), a phenylpiperazine antidepressant such as nefazodone (Serzone®), a piperazino-azepine antidepressant such as mirtazapine (Remeron®), mixtures thereof, and the like.

In yet other embodiments, the drug may be an NMDA receptor antagonist. Phencyclidine, ketamine, and dextromethorphan, are used as recreational drugs. At subanesthetic doses, however, these drugs have mild stimulant effects, and these agents have shown promise for the treatment of conditions that involve excitotoxicity, including traumatic brain injury, stroke, and neurodegenerative diseases such as Alzheimer's, Parkinson's, and Huntington's.

Additionally, the drug may be an agent that treats neuropathic/neurogenic pain (pain that arises from nerve dysfunction and not as a result of injury, e.g., trigeminal neuralgia), such as carbamazepine, gabapentin, topiramate, zonisamide, phenytoin, desipramine, amitriptyline, imipramine, doxepin, protriptyline, pentoxifylline, and hydroxyzine.

In other embodiments, the drug treats insomnia, such as zolpidem (Ambien®).

In other embodiments, the drug treats fatigue. Such drugs include central nervous system stimulants such as pemoline (Cylert®) and Modafinil (Provigil®).

In yet other embodiments, the drug treats vertigo, nausea and/or dizziness, such as meclizine (Antivert®), dimenhydrinate (dramamine), prochlorperazine (Compazine®), scopolamine (Transderm®) and diphenhydramine (Benadryl®). In yet other embodiments, the drug is a serotonin-norepinephrine reuptake inhibitor (SNRI), such as Desvenlafaxine (Pristiq®), Duloxetine (Cymbalta®), Milnacipran (Ixel®, Savella®), Venlafaxine (Effexor®), mixtures thereof, and the like.

In yet other embodiments, the drug is a tricyclic antidepressant (TCA), such as Amitriptyline (Elavil®), Butriptyline (Evadene®, Evadyn®e), Clomipramine (Anafranil®), Desipramine (Norpramin®, Pertofrane), Dosulepin (Prothiade), Doxepin (Adapin, Sinequan), Imipramine (Tofranil®), Lofepramine (Feprapax®, Gamanil®, Lomont®), Nortriptyline (Aventyl®, Nortrilen®, Pamelor®), Protriptyline (Vivacti®l), Trimipramine (Surmontil®), mixtures thereof, and the like.

In yet other embodiments, the drug is a tetracyclic antidepressant, such as Amoxapine (Asendin®), Maprotiline (Ludiomil®), Mianserin (Tolvon®), mixtures thereof, and the like.

In yet other embodiments, the drug is an atypical antipsychotic, such as Ziprasidone (Geodon®, Zeldox®), Nefazodone (Serzone®), and the like.

In yet other embodiments, the drug is an anti-convulsant or anti-epileptic drug such as arylsulfonimide analogues such as Acetazolimide (Diamox)®, tricyclic iminostilbene derivatives such as carbamazepine (Tegreto®), benzodiazepines such as clonazepam (Klonopin®), clorazepate dipotassium (Tranxene®), lorazepam (Ativan®) and diazepam (Valium®), carboxylic acid derivatives such as valproic acid (Depakene®) and divalproex sodium (Depakote®), succinimide derivatives such as ethosuximide (Zarontin®), carbamate esters of 2-phenyl-1,3-propanediol such as felbamate (Felbatol®), hydantoins such as phenytoin (Dilantin®), phenytoin sodium (Dilantin®) and fosphenytoin sodium (Cerebyx®), structural analogues of GABA such as gabapentin (Neurontin®) and pregabalin (Lyrica®), phenyltriazines such as lamotrigine (Lamictal®), pyrrolidine derivatives such as levitiracetam (Keppra®), tricyclic iminostilbene derivatives such as oxcarbezepine (Trileptal), barbiturates such as Phenobarbital, desoxybarbiturates such as primidone (Mysoline®), nipecotic acid derivatives such as tiagabine hydrochloride (Gabitril®), sulfamated monosaccharides such as topiramate (Topamax®), oxazolidinedione derivatives such as trimethadione (Tridione®), and methanesulfonamides such as zonisamide (Zonigran®). Additional drugs such as Retigabine® (Valeant Pharmaceuticals), Lacosamide® (Schwarz Biosciences), and Perampanel® (Eisai) are in development as anti-epileptics and neuromodulators for other associated neurological, pain, and psychiatric conditions, and thus are further examples of potentially useful drugs in the present invention.

In yet other embodiments, the drug is an analgesic/antiinflammatory agent such as acetaminophen; prednisone, solumedrol, and other steroids; naproxen, aspirin, voltaren, ketoprofen, ibuprofen, nabumetone, and other NSAID's. The NSAID may be COX-1, COX-2 or mixed COX-1/COX-2 inhibitors. Examples of COX-2 inhibitors include oxicam, meloxicam, and the more selective celecoxib, rofecoxib, valdecoxib, parecoxib and etoricoxib. Further examples of corticosteroids include methylprednisolone, prednisolone, dexamethasone, and adreno-corticotrophic hormone(ACTH), corticotropin.

Additionally, the drug may be an agent that treats neuropathic/neurogenic pain (pain that arises from nerve dysfunction and not as a result of injury, e.g., trigeminal neuralgia), such as carbamazepine, gabapentin, topiramate, zonisamide, phenytoin, desipramine, amitriptyline, imipramine, doxepin, protriptyline, pentoxifylline, and hydroxyzine, mixtures thereof, and the like.

In other embodiments the drug is partial agonist at the $\alpha 4^\beta 2$ nicotinic acetylcholine receptors, used for smoking cessation. The characteristics of varenicline (Chantix®), having a molecular weight (MW) of 261 and high water solubility, make it ideal for topical delivery. The usual adult dose of varenicline for smoking cessation is: Days 1-3: 0.5 mg orally once a day; Days 4-7: 0.5 mg orally twice a day; Days 8-end of treatment: 1 mg orally twice a day, for one or two twelve week cycles of treatment. Another agent in this class is cytosine (Tabex®), which is a plant alkaloid and is marketed for smoking cessation in Europe.

In other embodiments, the drug is 4-aminopyridine (4-AP; also known as Fampridine®) or a pharmaceutically acceptable derivative thereof. This drug has been shown to have the ability to improve the communication between damaged nerves, which may result in increased neurological function in the treatment of conditions such as multiple sclerosis (MS). An example of another such drug is 3,4 diaminopyridine.

In yet other embodiments, the drug is an appetite suppressant, such as Sibutramine (Meridia®, Reductil®), which is a centrally acting serotonin-norepinephrine reuptake inhibitor that is structurally related to amphetamines but having a distinct mechanism of action. Other potentially useful drugs for anti-obesity include Rimonabant (Acomplia®), substances related to amphetamine, such as phentermine and/or fenfluramine and/or dexfenfluramine, (the combination popularly referred to phenfen) may also be useful in the treatments of the present invention. It is believed that the present method of treatment would avoid the potential heart value damage found with these combinations when administered orally.

In other embodiments, the drug is useful for the treatment of Dementia/Alzheimer's disease, such as Aricept®/donepezil, Exelon®/rivastigmine, Reminyl®/Razadyne®/galantamine, and Namenda®/memantine, their naturally occurring counterparts, and mixtures thereof.

In other embodiments, the drug is useful for the treatment of ADD, ADHD, and similar conditions, and the drug is, for example, one or more amphetamine derivatives or isomers thereof, such as lisdexamfetamine (Vyvance®), Adderall® (75% d-amphetamine and 25% l-amphetamine, methylphenidate (Ritalin®, Concerta®), dextroamphetamine, dexmethylphenidate hydrochloride (Focalin®), Ritalin®), atomoxetine (Strattera®), mixtures thereof, and the like.

It has been observed and reported that patients given apomorphine injections regularly developed penile erections. Some of these patients had problems of impotence with erectile dysfunction. These patients reported improvement in sexual function with apomorphine injections. Animal studies suggest central dopamine D2 receptor stimulation may be mediating this effect. It is also known that the male sexual response is related to the autonomic nervous system: primarily the parasympathetic component for erection and, the sympathetic for ejaculation. This suggests the possible role of apomophine delivered as TRNA BONATH therapy for the treatment of sexual dysfunction in Parkinson's disease as well as from other conditions. Thus, the present invention also encompasses the use of apomorphine and other dopamine agonists (e.g., as set forth above), as well as sildenafil (Viagra®), vardenafil (Levitra®), tadalafil (Cialis®), alprostadil (Prostin®), and mixtures of any of the foregoing.

Formulations

All currently approved therapies for the conditions described above reach the central nervous system through the systemic circulation. Cerebral blood flow to brainstem structures is through the posterior circulation, via the vertebral and basilar arteries and their branches. In view of the undesirable side-effects associated with this form of drug delivery to the brain, it makes sense that targeted regional delivery to the brainstem is sought. Topical delivery of currently used drugs compounded in an appropriate "dermal penetration enhancer" and applied in cream/gel form or as a sustained-release patch at the posterior cervical region (back of the neck) at the hairline is such a method. Lipoderm® is an example of an effective commercially available compounding medium. However, one skilled in the art will recognize that topical carriers meeting the specific chemical requirements of an individual drug can be formulated for maximum efficiency in topical delivery.

The formulations of the present invention are prepared such that the drug(s) may be delivered acutely as single dose applications as cream/gel/ointment or as a sustained release topical patch, depending on the condition treated and associated symptom complex in the individual patient. The critical point, again, is in the location of the application: at the back of neck at the hair-line for access to posterior cervical afferents with free nerve endings under the surface of the skin. Through feedback connections with vagal and trigeminal afferent systems, this results in ultimate effect on brainstem structures.

By virtue of the method of treatment described herein, the disease state/condition to be treated may be treated much faster and more effectively than such prior art modes of administration.

In certain embodiments of the present invention, the method of treating a human patient comprises applying a topical formulation which comprises a drug suitable for topical administration, which is useful for the treatment of a disease state or condition treatable via the topical brainstem afferent stimulation (de-afferentation) drug therapy described herein.

The methods of the present invention may also, if desired, involve pre-treatment of the skin with an enhancer to increase the permeability of the skin to the applied drug. The methods of the present invention may include pre-treatment or "prepping" of the skin area with a substance that opens up the skin pores. Additionally, the methods of the present invention may include, if desired, pre-treatment or "prepping" of the skin with an alcohol swab or the like to rid the area of dirt, makeup, oil, and the like, prior to application of the drug.

In certain embodiments, the topical formulation of the present invention comprises a drug in an amount which is therapeutically effective when administered topically at the at the back of neck at the hair-line for access to posterior cervical afferents with free nerve endings under the surface of the skin, but which provides a plasma concentration which is subtherapeutic if orally administered.

In certain embodiments, by applying the formulation of the present invention comprising a dose of drug at the back of neck at the hair-line for access to posterior cervical afferents with free nerve endings under the surface of the skin, it may be possible for the use of lower doses of drug or faster relief of the headache than if applied to the trunk or limbs of a human patient, and the lower plasma levels of drug which result from lower doses may thereby reduce unwanted side effects of the drug.

The topical formulations of the present invention (e.g., ointment, gel, cream, or the like), must be suitable for topical administration of a drug, i.e., must contain pharmaceutically acceptable excipients compatible with application to the skin tissue, and may optionally contain a sufficient amount of an enhancer composition as described hereinafter.

In certain embodiments, in addition to the drug (e.g., dopamine agonist), the topical formulations and/or transdermal therapeutic systems of the present invention may include at least one adjuvant such as a penetration enhancer, antioxidant, stabilizer, carrier, or vehicle. Additionally or alternatively, the present invention may include the application of electric current (iontophoresis) for enhancing permeation of the dopamine agonist.

In certain embodiments, the topical formulations comprising a drug in an ointment, gel, cream or the like, will typically contain on the order of about 0.001 to about 80% by weight, preferably 0.01 wt. % to 50 wt. % drug, and about 0 wt. % to about 50.0 wt. %, preferably from about 1 wt. % to about 30 wt. % of a permeation enhancer composition, with the remainder of the composition comprising a carrier or vehicle. In certain preferred embodiments, the drug is included in a cream or gel or ointment in a concentration of, e.g., 1 mg drug/ml of carrier (e.g., Lipoderm). However, it is to be understood that one skilled in the art can increase the amount of carrier or change the carrier and maintain or improve efficacy of the topical formulation for TRNA therapy.

In certain embodiments, the topical formulations comprising a dopamine agonist in an ointment, gel, cream or the like, will typically contain on the order of about 0.001 to about 80% by weight, preferably 0.01 wt. % to 50 wt. % dopamine agonist, and about 0 wt. % to about 50.0 wt. %, preferably from about 1 wt. % to about 30 wt. % of a permeation enhancer composition, with the remainder of the composition comprising a carrier or vehicle. In certain preferred embodiments, the dopamine agonist is apomorphine and is included in a cream or gel or ointment in a concentration of, e.g., 1 mg drug/ml of carrier (e.g., Lipoderm). However, it is to be understood that one skilled in the art can increase the amount of carrier or change the carrier and maintain or improve efficacy of the topical formulation for TRNA therapy. In certain preferred embodiments, the drug is applied as a unit dose at the BONATH in immediate release form (e.g., cream, ointment or gel) for acute treatment with a dopamine agonist as would be beneficial to a person suffering from, e.g., Parkinson's disease or impotence/male erectile dysfunction. In such instances, it is preferred that the concentration of dopamine agonist included in the unit dose is from about 0.25 mg to about 4 mg, based on apomorphine, or an therapeutically equivalent amount of another dopamine agonist as described herein.

Suitable permeation enhancers may also be included in the formulations. Such enhancers include, but are not limited to, dimethylsulfoxide (DMSO), N,N-dimethylacetamide (DMA), decylmethylsulfoxide (C10 MSO), polyethylene glycol monolaurate (PEGML), propylene glycol (PG), PGML, glycerol monolaurate (GML), lecithin, the 1-substituted azacycloheptan-2-ones, particularly 1-n-dodecylcyclazacycloheptan-2-one (available under the trademark Azone® from Whitby Research Incorporated, Richmond, Va.), alcohols, and the like. The permeation enhancer may also be a vegetable oil as described in U.S. Pat. No. 5,229,130 to Sharma. Such oils include, for example, safflower oil, cotton seed oil and corn oil.

Additional enhancers for use in conjunction with the present invention are lipophilic compounds having the formula [RCOO]n R', wherein n is 1 or 2 and R is C1-C16 alkyl optionally substituted with 1 or 2 hydroxyl groups, and R' is hydrogen or C1-C16 alkyl optionally substituted with 1 or 2 hydroxyl groups. Within this group, a first subset of compounds are represented by the formula [CH3 (CH2)m COO]n R' in which m is an integer in the range of 8 to 16, n is 1 or 2, and R' is a lower alkyl (C1-C3) residue that is either unsubstituted or substituted with one or two hydroxyl groups. Preferred enhancers within this group include an ester which is a lower alkyl (C1-C3) laurate (i.e., m is 10 and n is 1) such as "PGML". It will be appreciated by those skilled in the art that the commercially available material sold as "PGML" is typically although not necessarily a mixture of propylene glycol monolaurate itself, propylene glycol dilaurate, and either propylene glycol, methyl laurate, or both. Thus, the terms "PGML" or "propylene glycol monolaurate" as used herein are intended to encompass both the pure compound as well as the mixture that is typically obtained commercially. Also within this group is a second subset of compounds, namely, esters of fatty alcohols represented by the formula CH3 (CH2)m-O—CO—CHR1R2, in which R1 and R2 are independently hydrogen, hydroxyl, or lower alkyl (C1-C3), and m is as above. Particularly preferred enhancers within this group are lauryl lactate and myristyl lactate. In addition, a third subset of compounds within this group are analogous fatty acids, i.e., acids having the structural formula CH3 (CH2)m COOH where m is as above. A particularly preferred acid is lauric acid.

Other enhancer compositions are wherein a lipophilic compound as just described, particularly PGML is combined with a hydrophilic compound, such as a C2-C6 alkanediol. One preferred hydrophilic enhancer within this group is 1,3-butanediol. Such enhancer compositions are described in detail in PCT Publication No. WO 95/05137, published Feb. 23, 1995, herein incorporated by reference. Another hydrophilic enhancer that may be included in these compositions is an ether selected from the group consisting of diethylene glycol monoethyl ether (Transcutol) and diethylene glycol monomethyl ether. Such enhancer compositions are described in detail in U.S. Pat. Nos. 5,053,227 and 5,059,426 to Chiang et al., the disclosures of which are herein incorporated by reference.

Other enhancer compositions may include mixture or combinations of any of the aforementioned enhancers, and the like.

In certain embodiments the topical formulation may include at least one water-insoluble, pharmacologically approved, alkyl cellulose or hydroxyalkyl cellulose, and the like. Alkyl cellulose or hydroxyalkyl cellulose polymers for use in this invention include ethyl cellulose, propyl cellulose, butyl cellulose, cellulose acetate, hydroxypropyl cellulose, hydroxybutyl cellulose, and ethylhydroxyethyl cellulose, alone or in combination. In addition, a plasticizer or a cross linking agent may be used to modify the polymer's characteristics. For example, esters such as dibutyl or diethyl phthalate, amides such as diethyldiphenyl urea, vegetable oils, fatty acids and alcohols such as acid oleic and myristyl may be used in combination with the cellulose derivative.

In certain embodiments, the topical formulation may further include hydrocarbons such as liquid paraffin, vaseline, solid paraffin, microcrystalline wax, etc.; higher aliphatic alcohols such as cetyl alcohol, hexadecyl, alcohol, stearyl alcohol, oleyl alcohol, etc.; esters of higher fatty acids with higher alcohols such as beeswax, etc.; esters of higher fatty acids with lower alcohols such as isopropyl myristate, isopropyl palmitate, etc.; vegetable oils, modified vegetable oils, hydrous lanolin and its derivative, squalene, squalane; higher fatty acids such as palmitic acid, stearic acid, etc. and the like.

In certain embodiments, the topical formulation may further include emulsifiers and dispersing agents which include, for example, anionic, cationic and nonionic surfactants. Nonionic surfactants are preferred because of their low levels of irritation to skin. Typical of nonionic surfactants are fatty acid monoglycerides such as glyceryl monostearate, etc.; sorbitan fatty acid esters such as sorbitan monolaurate, etc.; sucrose fatty acid esters; polyoxyethylene fatty acid esters such as polyoxyethylene stearate, etc.; and polyoxyethylene higher alcohol ethers such as polyoxyethylene cetyl ether, polyoxyethylene oleyl ether, etc.

In certain preferred embodiments, the topical TRNA formulation is aqueous-based.

In certain embodiments of the present invention, the topical formulation may include a gelling agent such as methylcellulose, ethylcellulose, hydroxyethylcellulose, hydroxypropyl-cellulose, hydroxypropylmethylcellulose, carboxymethylcellulose, carbomer, and the like. Examples of pharmaceutical compositions which rely upon an aqueous gel composition as a vehicle for the application of a drug are U.S. Pat. Nos. 4,883,660; 4,767,619; 4,511,563; 4,861,760; and 5,318,780, the disclosures of which are herein incorporated by reference.

The topical formulation may further include one or more preservatives, stabilizers, or anti-oxidants.

Examples of preservatives that may be used in a formulation according to the present invention include, but are not limited to, bacteriostatic compounds and other preservatives suitable for topical administration including various alcohols, sorbic acid and salts and derivatives thereof, ethylenediamine, monothioglycerol, and thimerosal.

Examples of stabilizers that may be present in a formulation according to the present invention include pH buffers suitable for topical administration, complexing agents, chelating agents and the like.

Examples of anti-oxidants that may be used in a formulation according to the present invention include ascorbic acid and its derivatives, e.g., ascorbyl palmitate, as well as butylated hydroxyanisole, butylated hydroxytoluene, sodium bisulfite, sodium metabisulfite, and others.

Other adjuvants that may be included in the drug formulation include carriers, tackifiers, pigments, dyes, and other additives that do not adversely affect the mechanical or adhesive properties of the formulation.

"Carriers" or "vehicles" as used herein refer to carrier materials suitable for transdermal drug administration, and include any such materials known in the art, e.g., any liquid, gel, emulsion, solvent, liquid diluent, solubilizer, or the like, which is nontoxic and which does not interact with other components of the composition in a deleterious manner. The term "carrier" or "vehicle" as used herein may also refer to stabilizers, crystallization inhibitors, dispersing agents or other types of additives useful for facilitating transdermal drug delivery. It will be appreciated that compounds classified as "vehicles" or "carriers" may sometimes act as permeation enhancers, and vice versa, and, accordingly, these two classes of chemical compounds or compositions may sometimes overlap.

Carrier materials suitable for use in the instant compositions include those well-known for use in the cosmetic and medical arts as bases for ointments, lotions, salves, aerosols, suppositories and the like. Suitable carriers include, for example, water, liquid alcohols, liquid glycols, liquid polyalkylene glycols, liquid esters, liquid amides, liquid protein hydrolysates, liquid alkylated protein hydrolysates, liquid lanolin and lanolin derivatives, and like materials commonly employed in cosmetic and medicinal compositions. Other suitable carriers herein include for example alcohols, including both monohydric and polyhydric alcohols, e.g., ethanol, isopropanol, glycerol, sorbitol, 2-methoxyethanol, diethyleneglycol, ethylene glycol, hexyleneglycol, mannitol, and propylene glycol; ethers such as diethyl or dipropyl ether; polyethylene glycols and methoxypolyoxyethylenes (carbowaxes having molecular weight ranging from 200 to 20,000); polyoxyethylene glycerols, polyoxyethylene sorbitols, stearoyl diacetin, and the like.

In certain preferred embodiments of the present invention where it is desired that the drug (.e.g., dopamine agonist) is administered chronically, the formulations of the present invention may be formulated as a transdermal delivery system (also referred to herein as a transdermal therapeutic system) such as a transdermal patch, a transdermal plaster, a transdermal disc, iontophoretic transdermal device, or the like. Such formulations are recognized by those skilled in the art as providing a release of drug and absorption into the skin of the patient in a sustained manner over an extended period of time (e.g., 1-7 days). In such embodiments of the present invention, the transdermal delivery system comprises, e.g., a dopamine agonist contained in a reservoir or a matrix, and an adhesive which allows the transdermal patch to adhere to the skin, allowing the passage of the active agent from the transdermal patch through the skin of the patient. In preferred embodiments, the transdermal patch is applied topically at the back of the neck at the hairline ("BONATH") so as to achieve topical regional neuro-affective therapy ("TRNA THERAPY") as described herein. In embodiments in which the drug is contained in a transdermal patch, it is contemplated that the drug will be absorbed more slowly and the transdermal patch will provide a sustained release and prolonged therapeutic effect, as compared, e.g., to a cream or ointment intended to provide an immediate release of the drug and rapid onset of the TRNA therapy.

In certain embodiments, the transdermal delivery devices, as well as other transdermal delivery systems in accordance with the invention can be made in the form of an article such as a tape, a patch, a sheet, a dressing or any other form known to those skilled in the art. Generally the device will be in the form of a patch of a size suitable to deliver a unit dose of serotonin agonist through the skin. The drug may be introduced into a transdermal therapeutic system in different forms (solid, in solution, in dispersion); it may also be microencapsulated.

In certain embodiments the present invention provides a transdermal therapeutic system comprising a drug (e.g., serotonin agonist) in an amount that would provide sub-therapeutic plasma levels if administered orally, but is therapeutically effective when administered via transdermal delivery at the headache region.

A transdermal delivery system for use in accordance with the present invention can also be constructed with an enhancer composition and other ingredients described hereinabove with respect to the topical formulation. Preferably, the transdermal delivery system is formulated for the prolonged delivery of a drug (e.g., dopamine agonist) as would be beneficial to a person suffering from, e.g., Parkinson's disease or impotence/male erectile dysfunction. The targeted skin flux for delivery of a particular drug can be achieved by adjusting vehicle composition and vehicle loading, as well as by adjusting the surface area through which the compositions are administered to skin.

In certain preferred embodiments, the transdermal delivery system (e.g., patch) is formulated to deliver from about 4 mg to about 50 mg of the dopamine agonist per each 24 hours through the skin of the patient, based on apomorphine, or a therapeutically equivalent amount of a suitable alternative dopamine agonist as described herein. In embodiments in which the transdermal delivery system is intended to be applied to the skin at the BONATH for multiple days, the transdermal delivery system (e.g., patch) is formulated to provide a flux rate over the useful life of the system such that a similar amount (e.g., mean dose) is delivered on a daily basis until the system is removed and replaced with a fresh system.

The transdermal delivery system used in the present invention may be prepared, for example, in accordance with U.S. Pat. Nos. 5,069,909; 4,806,341; 5,026,556; 4,588,580; 5,016,652; 3,598,122; 4,144,317; 4,201,211; 4,262,003; and 4,379,454; all of which are incorporated herein by reference.

Additionally, the transdermal delivery system used in the present invention may be in accordance with U.S. Pat. No. 6,689,379, hereby incorporated by reference, which system is a matrix or reservoir system which comprises: at least one pharmaceutical active agent selected from the group consisting of basic pharmaceutical active agents and neutral pharmaceutical active agents (such as rivastigmine); and a pressure-sensitive adhesive comprising a polyacrylate polymer, wherein said polyacrylate polymer has a polyacrylate backbone containing monomer units selected from the group consisting of acrylic acid, methacrylic acid and ester derivatives of acrylic or methacrylic acid, and said monomer units comprise at least 50% (w/w) relative to a mean polymer mass of said polyacrylate polymer, a total amount of monomers selected from the group consisting of non-esterified acrylic acid and non-esterified methacrylic acid is 0.5 to 10.0% (w/w) relative to the mean polymer mass of said polyacrylate polymer, and the carboxyl groups of said non-esterified acrylic and methacrylic acid monomers are present stoichiometrically at 5 to 100% in the form of alkali salts or alkaline-earth salts, said salts being reaction products of a neutralization reaction of an alcoholic solution of an alkaline hydroxide or an alkaline-earth hydroxide with said acrylate polymer(s), or of a neutralization reaction of an alkali alcoholate or an alkaline-earth alcoholate with said acrylate polymer(s).

In certain embodiments, the dosage form can be a transdermal patch comprising a laminated composite for administering the drug (e.g., dopamine agonist) to an individual transdermally comprising: (a) a polymer backing layer that is substantially impermeable to the dopamine agonist; and (b) a reservoir layer comprising a water-base acrylate pressure-sensitive adhesive, 1 to 12% by weight serotonin agonist and 2 to 25% by weight of a permeation enhancer comprising propylene glycol monolaurate in combination with capric acid or oleic acid, wherein the skin contact area of the composite is 10 to 100 cm2.

The dosage form can be a transdermal patch comprising (a) a polar solvent material selected from the group consisting of C3-C4 diols, C3-C6 triols, and mixtures thereof; and (b) a polar lipid material selected from the group consisting of fatty alcohol esters, fatty acid esters, and mixtures thereof; wherein said polar solvent material and said polar lipid material are present in a weight ratio of solvent material:lipid material of from about 60:40 to about 99:1.

In certain embodiments, the dosage form also comprises a transdermal plaster comprising: (1) a film layer which comprises a polyester film of 0.5 to 4.9 microns thickness, 8 to 85 g/mm strength, respectively in the two directions intersecting substantially at right angles, 30 to 150% elongation, in the two directions intersecting substantially at right angles and an elongation ratio of A to B of 1.0 to 5.0, wherein A and B represent data in two directions intersecting at right angles, and A is greater than B, and wherein said polyester film comprises 0.01 to 1.0% by weight, based on the total weight of said polyester film, of solid fine particles in which (a) the average particle size is 0.001 to 3.0 microns, and (b) the average particle size is substantially not more than 1.5 times the thickness of said polyester film; and (2) an adhesive layer (a) which is composed of an adhesive containing said serotonin agonist and further wherein said adhesive layer (a) is laminated on said film layer over the surface in a 2 to 60 microns thickness.

In certain embodiments, the dosage form can be a transdermal disc comprising: (a) a backing layer which is substantially impervious to the dopamine agonist; and (b) a polymer matrix disc layer which is adhered to said backing layer and which has microdispersed therein said serotonin agonist, said polymer being bioacceptable and permitting said serotonin agonist to be transmitted for transdermal absorption, the dopamine agonist being stable in said polymer matrix.

In certain embodiments, the topical formulation or transdermal therapeutic system may further comprise another active ingredient in combination with the first drug (e.g., dopamine agonist), e.g., analgesics, antimimetics, psychopharmacologic agents, or sedatives.

The present invention is contemplated to encompass all transdermal formulations, e.g., the technologies described above, with the inclusion of a drug (e.g., dopamine agonist(s)), such that the administration of a drug useful for treatment of disease state or condition in humans via topical brainstem afferent stimulation (de-afferentation) therapy via topical administration. Therefore, modifications of the invention via, e.g., the choice and/or amount of drug are considered to be obvious variations of this disclosure and within the scope of the appended claims.

The present invention also contemplates the administration of the drug (e.g., dopamine agonist) directly below the skin to affect direct brainstem afferent stimulation to the free nerve endings under the epidermis. Such administration may be effected as an injection (e.g., subcutaneous injection) or implantation of the drug in immediate release or sustained release form. It will be appreciated by those skilled in the art that providing the drug in sustained release form and administering it in a suitable form below the skin may provide benefits, including less frequent administration (e.g., in chronic therapy).

In certain embodiments of the invention, the drug (e.g., dopamine agonist) can be formulated for controlled or sustained delivery at the BONATH via incorporation into a biocompatible and implantable polymer which can be in the form of microparticles or an implantable insert, or a liquid that forms a gel or colloid or a semi-solid after injection (thereby encapsulating the drug and allowing it to be released in a prolonged and controlled manner at the desired site). For chronic conditions (e.g., Parkinson's) or desired prolonged effect, it is contemplated that a drug depot or reservoir may be created under the skin at the BONATH, which then provides a sustained release of the drug in proximity to the desired nerve endings and which may be replenished or replaced at the end of the dosing interval. It is contemplated that such administrations of the drug (e.g., dopamine agonist) may provide a prolonged therapeutic effect for at least about 3 days, preferably at least about 7 days, or longer. Such formulations may be administered in certain embodiments as, for example, a subcutaneous depot.

Implants are placed subcutaneously by making an incision in the skin and forcing the implants between the skin and the muscle. At the end of their use, if not dissolved, these implants are surgically removed. U.S. Pat. No. 4,244,949, hereby incorporated by reference, describes an implant which has an outer matrix of an inert plastic such as polytetrafluoroethylene resin. Examples of this type of implantable therapeutic system are Progestasert IUD and Ocusert system. It is contemplated that such systems can be appropriately modified by one skilled in the art for use in conjunction with the present invention. A commercially available product, Norplant®, which is an implant having a core containing levonorgestrel as the active substance, and where the core it surrounded by a membrane of a silicone elastomer of poly(dimethylsiloxane) (PDMS). Another preparation of this kind is Jadelle®, in which the core is a poly(dimethylsiloxane) based matrix with levonorgestrel dispersed therein. The membrane is an elastomer made from PDMS and silica filler, which, besides giving necessary strength properties to the membrane, also retards the permeation of the active agent through the membrane. U.S. Pat. No. 3,854,480, hereby incorporated by reference, describes a drug delivery device, e.g. an implant, for releasing a drug at a controlled rate for a prolonged period of time. The device has a core of a matrix in which the drug is dispersed. The core is surrounded by a membrane that is insoluble in body fluids. The core matrix as well as the membrane are permeable to the drug by diffusion. The materials of the core and the membrane are chosen so that the drug diffuses through the membrane at a lesser rate than through the core matrix. Thus, the membrane controls the release rate of the drug. As a suitable polymer for the core matrix is mentioned poly(dimethylsiloxane) (PDMS), and as suitable polymers for the membrane are mentioned polyethylene and a copolymer of ethylene and vinyl acetate (EVA). It is contemplated that the above systems may be adapted by one skilled in the art to deliver the drug (e.g., dopamine agonists) in accordance with the present invention.

One device which may be adapted by one skilled in the art for use in the present invention is described in U.S. Pat. No. 5,968,542 (Tipton), hereby incorporated by reference, which describes a high viscosity liquid controlled delivery system as a medical or surgical device is provided that includes: (i) a non-polymeric, non-water soluble liquid carrier material (HVLCM) of viscosity of at least 5,000 cP at 37.degree. C. that does not crystallize neat under ambient or physiological conditions; and, optionally, (ii) a substance to be delivered.

The pharmaceutical compositions suitable for injectable use in accordance with this invention include sterile aqueous solutions or dispersions and sterile powders or lyophopolysates for the extemporaneous preparation of sterile injectable solutions or dispersions. The dosage forms must be sterile and it must be stable under the conditions of manufacture and storage. The carrier for injectable formulations is typically water but can also include ethanol, a polyol (for example, glycerol, propylene glycol and liquid polyethylene glycol), mixtures thereof, and vegetable oil.

Injectable formulations used in the present invention can also be formulated as injectable prolonged release formulations in which the active compound is combined with one or more natural or synthetic biodegradable or biodispersible polymers such as carbohydrates, including starches, gums and etherified or esterified cellulosic derivatives, polyethers, polyesters, polyvinyl alcohols, gelatins, or alginates. Such dosage formulations can be prepared for example in the form of microsphere suspensions, gels, or shaped polymer matrix implants that are well-known in the art for their function as "depot-type" drug delivery systems that provide prolonged release of the biologically active components. Such compositions can be prepared using art-recognized formulation techniques and designed for any of a wide variety of drug release profiles.

One example of a useful formulation which may be used in the methods of the present invention for providing a prolonged duration of action is described in U.S. Pat. No. 7,332,503 (Wikstrom, et al.), hereby incorporated by reference. Therein, apomorphine derivatives and the physiologically acceptable salts thereof as well as formulations thereof are described which provide a prolonged duration of action. The apomorphine pro-drugs can be suspended (as a neat oil or as crystals, or dissolved in a suitable and pharmaceutically acceptable solvent (e.g. water, ethanol, DMSO, i-PrOH or benzylbenzoate)) in a pharmaceutically acceptable depot oil (e.g. viscoleo, sesame oil or olive oil) and injected subcutaneously or intramuscularly with a syringe or a "pen injector".

Alternatively, these drugs may, in a suitable composition and with a suitable vehicle (penetration enhancer), be applied to a patch for transdermal administration. The composition could include also a local anesthetic (e.g. lidocaine) to avoid injection pain, in particular at intramuscular injections. In one embodiment, the composition is in the form of a patch or an ointment for transdermal administration. The patch or ointment preferably also comprises stabilizers, solubilizers and permeation activators to facilitate the passage of the active principle through the skin. In another preferred embodiment, the composition is in the form of a depot preparation for subcutaneous or intramuscular administration comprising an apomorphine derivative or the physiologically acceptable salt thereof dissolved or suspended in an oil. In certain embodiments, in addition to the apomorphine derivative, the formulation further contains a local anesthetic. The formulations described in the '503 patent can be modified as understood by one skilled in the art to contain other active drugs as described herein for use at the BONATH.

An injectable depot formulation is a dosage form, which is generally intended to have a therapeutic activity for 2 to 4 weeks after administration (e.g. neuroleptics like Fluphenazine decanoate in sesame oil). In order to maintain effective drug plasma levels the dosage form should release the drug at a more or less constant rate during the desired dosing interval. The difference between such prior art depots and depots used in the present invention is that the in accordance with the present invention, the drug is not needed to be absorbed into the systemic circulation.

A suitable form of depot preparation is the subcutaneous or intramuscular administration of an oil solution and/or oil suspension of a lipophilic drug. This gives a slow transport over the oil-biofluid interface and a slow dissolution in the biophase. Thus, when the drug is dissolved in a polar solvent (e.g. oils), which is non-miscible with the aqueous biological fluids, the drug has to be transported over the oil\water interface. When the oil/water partition coefficient is high, the transport will be slow. For very lipophilic drugs, the release from the oil phase may last for up to several weeks. The use of depot preparations such as those described herein may be used to deliver the drugs described herein at the BONATH.

The maximum volume of an oil solution/suspension to be injected intramuscularly or subcutaneously is 2-4 mL. This is feasible for the preparations of the aporphine derivatives of the present invention. The accumulated daily dose used in apomorphine s.c. therapy in Parkinson's disease is, e.g., 4-10 times about 1-4 mg (4-40 mg/day). For example, 2 mg Apomorphine HCl (or equivalent molar amount of another dopamine agonist(s), as the base or as a suitable salt or ionpair) may be dissolved in 1 mL of an oil (sesame oil, Viscoleo or another approved oil) and the mixture gently heated (max 50° C.) shaken in a test tube shaker and ultrasonicated for a short time (minutes) until the mixture becomes a homogeneous solution or suspension. If necessary, the dopamine agonist may first be dissolved in 50-300. mu.L DMSO, water, t-BuOH, PEG, benzylbenzoate, or another suitable and approved solvent or mixtures thereof, before adding the oil to a total volume of 1 mL.

Another example of a polymeric drug delivery system which may be adapted for use in the present invention by one skilled in the art is described in U.S. Pat. No. 5,601,835 (Sabel, et al.), hereby incorporated by reference, which describes a polymeric drug delivery system for delivery of any substance to the central nervous system. The delivery system is preferably implanted in the central nervous system for delivery of the drug directly to the central nervous system. These implantable devices can be used, for example, to achieve continuous delivery of dopamine, which cannot pass the blood brain barrier, directly into the brain for an extended time period. The implantable devices display controlled, "zero-order" release kinetics, a life time of a minimum of several weeks or months even when the devices contain water soluble, low molecular weight compounds, biocompatibility, and relative non-invasiveness. The polymeric devices are said to be applicable in the treatment of a variety of central nervous system disorders including Parkinson's disease, Alzheimer's dementia, Huntington's disease, epilepsy, trauma, stroke, depression and other types of neurological and psychiatric illnesses, and one skilled in the art can adapt that drug delivery system for delivering the drugs contemplated herein at the BONATH.

Yet another example of a system that may be adapted for use in the present invention is described in U.S. Pat. No. 5,601,835 (Sabel, et al.), hereby incorporated by reference, wherein a compound such as dopamine is encapsulated within a polymer to form a polymeric device, the device formed of a biocompatible polymer that is plastically deformable selected from the group consisting of ethylene vinyl acetate, polyurethanes, polystyrenes, polyamide, polyacrylamide, and combinations thereof having a non-porous polymer coating thereon with one or more openings, with limited water sorptivity and slight permeability to the passage of small, aqueous-soluble molecules, wherein said compound is linearly released (e.g., zero order release) from said polymeric device over a sustained period of time of at least 65 days at a predetermined level and rate when implanted in a patient at a specific site within the central nervous system where the compound is released directly into the central nervous system and the device remains essentially intact throughout the release period. The delivery device is a two-phase system which is manufactured using standard techniques such as blending, mixing or the equivalent thereof, following selection of the biologically active material to be delivered and an appropriate polymer for formation of the matrix. The general method of solvent casting as disclosed by Siegel and Langer, "Controlled release of polypeptides and other macromolecules", Pharmaceutical Research 1, 2-10 (1984), is modified so that drug is dispersed within the devices to create channels and pores to the surface for release of the drug at the desired rate. Where appropriate, a coating impermeable to the drug is placed over a portion of the drug containing polymer matrix to further regulate the rate of release. One skilled in the art can adapt that drug delivery system for delivering the drugs contemplated herein at the BONATH.

Yet another formulation which may used to deliver the drug (e.g., dopamine agonists) as set forth in the present invention at the BONATH is described in U.S. Pat. No. 7,314,636 (Caseres, et al.), hereby incorporated by reference, which describes injectable implants comprising glycolic acid and bio-compatible/bio-absorbable polymeric particles containing a polymer of lactic acid. The particles are small enough to be injected through a needle but large enough to avoid engulfment by macrophages. The injectables of this invention may be in a pre-activated solid form or an activated form (e.g., injectable suspension or emulsion).

It is further contemplated that the system described in U.S. Pat. No. 6,586,006 (Roser, et al.), hereby incorporated by reference, can be adapted by one skilled in the art for use in the present invention for delivery of drugs at the BONATH. Therein are described delivery systems suitable for delivery of bioactive materials to subcutaneous and intradermal, intramuscular, intravenous tissue, the delivery system being sized and shaped for penetrating the epidermis. The delivery systems comprises a vitreous vehicle loaded with the guest substance and capable of releasing the guest substance in situ at various controlled rates. Subdermal implantable therapeutic systems have also been formulated for slow release of certain pharmaceutical agents for extended periods of time such as months or years. A well-known example is Norplant® for delivery of steroid hormones.

In membrane permeation-type controlled drug delivery, the drug is encapsulated within a compartment that is enclosed by a rate-limiting polymeric membrane. The drug reservoir may contain either drug particles or a dispersion (or solution) of solid drug in a liquid or a matrix type dispersing medium. The polymeric membrane may be fabricated from a homogeneous or a heterogeneous nonporous polymeric material or a microporous or semipermeable membrane. The encapsulation of the drug reservoir inside the polymeric membrane may be accomplished by molding, encapsulation, microencapsulation, or other techniques. The implants release drugs by dissolution of the drug in the inner core and slow diffusion across the outer matrix. The drug release from this type of implantable therapeutic system should be relatively constant and is largely dependent on the dissolution rate of the drug in the polymeric membrane or the diffusion rate across or a microporous or semipermeable membrane. The inner core may substantially dissolve over time; however, in devices currently in use, the outer matrix does not dissolve.

Other implantable therapeutic systems involve matrix diffusion-type controlled drug delivery. The drug reservoir is formed by the homogeneous dispersion of drug particles throughout a lipophilic or hydrophilic polymer matrix. The dispersion of drug particles in the polymer matrix may be accomplished by blending the drug with a viscous liquid polymer or a semisolid polymer at room temperature, followed by cross-linking of the polymer, or by mixing the drug particles with a melted polymer at an elevated temperature. It can also be fabricated by dissolving the drug particles and/or the polymer in an organic solvent followed by mixing and evaporation of the solvent in a mold at an elevated temperature or under vacuum. The rate of drug release from this type of delivery device is not constant. Examples of this type of implantable therapeutic system are the contraceptive vaginal ring and Compudose implant. PCT/GB 90/00497 describes slow release glassy systems for formation of implantable devices. The described implants are bioabsorbable and need not be surgically removed. One skilled in the art can adapt these drug delivery systems for delivering the drugs contemplated herein at the BONATH.

In microreservoir dissolution-controlled drug delivery, the drug reservoir, which is a suspension of drug particles in an aqueous solution of a water-miscible polymer, forms a homogeneous dispersion of a multitude of discrete, unleachable, microscopic drug reservoirs in a polymer matrix. The microdispersion may be generated by using a high-energy-dispersing technique. Release of the drug from this type of drug delivery device follows either an interfacial partition or a matrix diffusion-controlled process. An example of this type of drug delivery device is the Syncro-Mate-C Implant.

Yet another formulation which may be adapted by one skilled in the art for use in the present invention is described in U.S. Pat. No. 6,576,263 (Truong, et al.), hereby incorporated by reference, which describes a preformed object for delivering an active agent for a subject, the preformed object including crosslinked protein, and methods of making and using.

Yet another formulation which may be adapted by one skilled in the art for use in the present invention is described in U.S. Pat. No. 6,287,588 (Shih, et al.), hereby incorporated by reference, which describes a composition and method for releasing a bio-active agent or a drug within a biological environment in a controlled manner. The composition is a dual phase polymeric agent-delivery composition comprising a continuous biocompatible gel phase, a discontinuous particulate phase comprising defined microparticles and an agent to be delivered. A microparticle containing a bio-active agent is releasably entrained within a biocompatible polymeric gel matrix. The bio-active agent release may be contained in the microparticle phase alone or in both the microparticles and the gel matrix. The release of the agent is prolonged over a period of time, and the delivery may be modulated and/or controlled. In addition, a second agent may be loaded in some of the microparticles and/or the gel matrix.

Yet another formulation which may be adapted by one skilled in the art for use in the present invention is described in U.S. Pat. No. 7,364,568 (Angel, et al.), hereby incorporated by reference, which describes a transdermal transport device includes a reservoir for holding a formulation of an active principle, and a needle with a bore extending along the length of the needle from a first end of the needle to a second end of the needle. The second end is substantially aligned to a plane parallel to a body surface of a biological body when the device is placed on the body surface. The device also includes an actuator which pumps the formulation through the bore of the needle between a target area of the body and the reservoir.

In yet other embodiments of the invention, the dopamine agonist is infused into the patient at the BONATH using technology known to be useful for infusing other drugs, such as an insulin pump. One such system, U.S. Pat. No. 7,354,420 (Steil, et al.), hereby incorporated by reference, describes a closed loop infusion system controls the rate that fluid is infused into the body of a user. The closed loop infusion system includes a sensor system, a controller, and a delivery system. The sensor system includes a sensor for monitoring a condition of the user. The sensor produces a sensor signal, which is representative of the condition of the user. The sensor signal is used to generate a controller input. The controller uses the controller input to generate commands to operate the delivery system. The delivery system infuses a liquid into the user at a rate dictated by the commands from the controller. Preferably, the sensor system monitors the glucose concentration in the body of the user, and the liquid infused by the delivery system into the body of the user includes insulin.

The present invention is contemplated to encompass all implantable or injectable formulations, e.g., the technologies described above, with the inclusion of a drug(s) (e.g., dopamine agonist(s)), such that the administration of a drug useful for treatment of disease state or condition in humans via topical brainstem afferent stimulation (de-afferentation) therapy. Therefore, modifications of the invention via, e.g., the choice and/or amount of drug are considered to be obvious variations of this disclosure and within the scope of the appended claims.

DETAILED DESCRIPTION OF PREFERRED EMBODIMENTS

The present invention will now be more fully described with reference to the accompanying examples. It should be understood, however, that the following description is illustrative only and should not be taken in any way as a restriction on the generality of the invention specified above.

Example 1

Topical Formulation

An aqueous based apomorphine cream was produced using Lipoderm® as the carrier. Lipoderm®/LIP is a commercially marketed compounding agent (from PCCA, Pharmaceutical Compounding Centers of America) having the following ingredients: Ethoxydiglycol, Water (Aqua), Glycerin, $C_{12-15}$Alkyl Benzoate, Glyceryl Stearate, Dimethicone, Cetearyl Alcohol, Cetearyl Glucoside, Polyacrylamide, Cetyl Alcohol, Magnesium Aluminum Silicate, Xanthan Gum, Aloe Vera (Aloe Barbadensis), Tocopheryl Acetate (Vitamin E Acetate), Prunus Amygadalus Amara (Bitter Almond) Kernel Oil, Vitis Vinifera (Grape) Seed Extract, Triticum Vulgare (Wheat) Germ Oil, Retinyl Palmitate (Vitamin A Palmitate), Ascorbyl Palmitate (Vitamin C Palmitate), Pro-Lipo Multi-emulsion Liposomic System, Tetrasodium EDTA, Phenoxyethanol, and Sodium Hydroxymethylglycinate. The concentration was 1 mg of apomorphine in 1 ml of Lipoderm. The concentration of apomorphine in the Lipoderm is 1 mg in 0.5 ml. Lipoderm is a whitish cream with no smell.

Example 2

Drug Using Formulation of Example 1

The efficacy of a topical apomorphine formulation was studied in six human patients suffering from Parkinson's disease who presented to the author's neurologic clinic at a certain stage of "off state" in their functioning. For each of these patients, an amount of the compounded cream prepared in accordance with Example 1 containing approximately 1 mg apomorphine (except 0.5 mg in one patient, E.K.) in 0.5 ml of compounding medium, was applied at the back of the neck at the hairline (BONATH) of the patient, so as to deliver the drug through topical regional neuro-affective (TRNA) therapy.

The patients, who were all on other routine Parkinson's medications, were evaluated using the UPDRS Motor Scale pre and post-treatment with the topical apomorphine. All patients had not had their respective Parkinson's medications for 4-6 hours and thus were in their "off-states". The UPDRS is an objectified observer-rated scale for evaluating Parkinson's disease that is used extensively in research. The scale looks at 27 items with 0 to 4 ratings for each: 0 for normal and 4 for the most extreme dysfunction. Accordingly, for a given patient, a UPDRS Motor Scale of 0 is normal and worse case scenario, 108 (27×4). A representative UPDS form is presented as Table 1 below:

TABLE 1

UNIFIED PARKINSON'S DISEASE RATING SCALE (UPDRS)
PART III: Motor Examination
(The score to be completed incrementally, i.e. 0.0, 0.5, 1.0, 1.5-4.0)

| | |
|---|---|
| 18. Speech: | 0. Normal |
| | 1. Slight loss of expression, diction, and/or volume |
| | 2. Monotone, slurred but understandable; moderately impaired |
| | 3. Marked impairment, difficult to understand |
| | 4. Unintelligible |
| 19. Facial Expression: | 0. Normal |
| | 1. Minimal hypomimia, could be normal "poker face" |
| | 2. Slight but definitely abnormal diminution of facial expression |
| | 3. Moderate hypomimia; lips parted some of the time |
| | 4. Masked or fixed facies with severe or complete loss of facial expression; lips parted ¼ inch or more |
| 20. Tremor at rest: | |
| 20a) Face, lips, chin | 0. Absent |
| 20b) Right hand | 1. Slight and infrequently present |
| 20c) Left hand | 2. Mild in amplitude and persistent, or moderate in amplitude, but only intermittently present |
| 20d) Right foot | 3. Moderate in amplitude and present most of the time |
| 20e) Left foot | 4. Marked in amplitude and present most of the time |
| 21. Action or postural tremor of hands: | |
| 21a) Right | 0. Absent |
| 21b) Left | 1. Slight; present with actions |
| | 2. Moderate in amplitude; present with action |
| | 3. Moderate in amplitude; present with posture-holding as well as with action |
| | 4. Marked in amplitude; interferes with feeding |
| 22. Rigidity (judged on passive movement of major joints with patient relaxed in sitting position; "cogwheeling" to be ignored: | |
| 22a) Neck | 0. Absent |
| 22b) Right upper | 1. Slight or detectable only when activated by mirror or other movement |
| 22c) Left upper | 2. Mild to moderate |
| 22d) Right lower | 3. Marked but full range of motion easily achieved |
| 22e) Left lower | 4. Severe; range of motion achieved with difficulty |
| 23. Finger taps (patient taps thumb with index finger in rapid succession with widest amplitude possible, each hand separately): | |
| 23a) Right | 0. Normal |
| 23b) Left | 1. Mild slowing and/or reduction in amplitude |

TABLE 1-continued

UNIFIED PARKINSON'S DISEASE RATING SCALE (UPDRS)
PART III: Motor Examination
(The score to be completed incrementally, i.e. 0.0, 0.5, 1.0, 1.5-4.0)

| | |
|---|---|
| | 2. Moderately impaired; definite and early fatiguing; may have occasional arrests in movement |
| | 3. Severely impaired; frequent hesitation in initiating movements or arrests in ongoing movement |
| | 4. Can barely perform the task |
| 24. Hands movements (patient opens and closes hands in rapid succession with widest amplitude possible, each hand separately): | |
| 24a) Right | 0. Normal |
| 24b) Left | 1 Mild slowing and/or reduction in amplitude |
| | 2. Moderately impaired; definite and early fatiguing; may have occasional arrests in movement |
| | 3. Severely impaired; frequent hesitation in initiating movements or arrests in ongoing movement |
| | 4. Can barely perform the task |
| 25. Rapid alternating movements of hand (pronation-supination movements of hands, vertically or horizontally, with as large an amplitude as possible, both hands simultaneously): | |
| 25a) Right | 0. Normal |
| 25b) Left | 1. Mild slowing and/or reduction in amplitude |
| | 2. Moderately impaired; definite and early fatiguing; may have occasional arrests in movement |
| | 3. Severely impaired; frequent hesitation in initiating movements or arrests in ongoing movement |
| | 4. Can barely perform the task |
| 26. Foot agility (patient taps heel on ground in rapid succersion, picking up entire leg; amplitude should be about 3 inches): | |
| 26a) Right | 0. Normal |
| 26b) Left | 1. Mild slowing and/or reduction in amplitude |
| | 2. Moderately impaired; definite and early fatiguing; may have occasional arrests in movement |
| | 3. Severely impaired; frequent hesitation in initiating movements or arrests in ongoing movement |
| | 4. Can barely perform the task |
| 27. Arising from chair(patient attempts to arise from a straight-backed wood or metal chair, with arms folded across chest): | |
| 27a) Right | 0. Normal |
| 27b) Left | 1 Slow or may need more than one attempt |
| | 3. Pushes self up from arms or seat |
| | 3. Tends to fall back and may have to try more than on time but can get up without help |
| | 4. Unable to arise without help |
| 28. Posture: | 0. Normal effect |
| | 1. Not quite erect, slightly stooped posture; could be normal for older person |
| | 2. Moderately stooped posture, definitely abnormal; can be slightly leaning to one side |
| | 3. Severely stooped posture with kyphosis; can be moderately leaning to one side |
| | 4. Marked flexion, with extreme abnormality of posture |
| 29. Gait: | 0. Normal |
| | 1. Walks slowly; may shuffle with short steps, but no festination or propulsion |
| | 2. Walks with difficulty but requires little or so assistance; may have some festination, short steps, or propulsion |
| | 3. Severe disturbance of gait; requires assistance |
| | 4. Cannot walk at all, even with assistance |
| 30. Postural stability (response to sudden posterior displacement produced by pull on shoulders while patient erect, with eyes open and feet slightly apart; patient is prepared): | 0. Normal |
| | 1. Retropulsion, but recovers unaided |
| | 2. Absence of postural response; would fall if not caught by examiner |
| | 3. Very unstable; tends to lose balance spontaneously |
| | 4. Unable to stand without assistance |
| 31. Body bradykinesia and hypokinesia (combining slowness, hesitancy, | 0. None |
| | 1. Minimal slowness, giving movement a deliberate character; |

TABLE 1-continued

UNIFIED PARKINSON'S DISEASE RATING SCALE (UPDRS)
PART III: Motor Examination
(The score to be completed incrementally, i.e. 0.0, 0.5, 1.0, 1.5-4.0)

| decreased arm swing, small amplitude and poverty of movement in general): | could be normal for some persons; possible reduced amplitude 2. Mild degree of slowness and poverty of movement that is definitely abnormal; alternatively, some reduced amplitude 3. Moderate slowness; poverty or small amplitude of movement 4. Marked slowness; poverty or small amplitude of movement |
|---|---|

The results of the study of Example 2 are set forth in Table 2 below:

TABLE 2

CLINICAL RESPONSE OF PARKINSON'S PATIENTS IN THE
"OFF-STATE" TO TOPICAL APOMORPHINE THERAPY:
CHANGE IN UPDRS MOTOR SCORES*

| Patient | Sex | Age | Duration Parkinsons | Current Parkinsons Medications | UPDRS Motor | | |
|---|---|---|---|---|---|---|---|
| | | | | | Pre | Post | Diff |
| E B | F | 86 | 8 years | Stalevo (Sinemet & Comtan) | 51 | 32 | 19 |
| G V | M | 87 | 12 | Stalevo | 38 | 18 | 20 |
| E K | F | 75 | 6 | Sinemet and Mirapex | 36 | 19 | 17 |
| W H | M | 88 | 11 | Sinemet and Mirapex | 51 | 31 | 20 |
| S K | F | 89 | 5 | Sinemet | 66 | 52 | 14 |
| I R | M | 64 | 10 | Sinemet, Mirapex and Amantatine | 57 | 34 | 23 |

*1.0 mg of apomorphine in 0.5 ml Lipoderm except 0.5 mg in patient (E. K.) Patients were re-examined within ½ hour after topical application.

As can be appreciated from Table 2, these 6 patients were fairly significantly affected by their disease. Within 15-30 minutes after application of the compounded apomorphine cream, they were all improved significantly. The average UPDRS score post-treatment was 31, indicating an average improvement of 19 points. The duration of improved functional state was observed to be from 2½ to 26 hours, representing the time period patients felt they were able to function off their usual Parkinson's medications due to the positive therapeutic effect of the topical apomorphine. After this period, all patients returned to their previous drug regimen, which consisted of taking Parkinson's medications 3-4 times per day. By their own accounts and those of their care-takers, their current therapy was considered sub-optimal. This was evident on formal clinical exam and documented by the UPDRS, as noted in Table 2. The only significant side-effects expressed were transient fatigue and dizziness, in patients E.K. and S.K.

Video-tape of pre and post-treatment states with topical apomorphine was performed on several patients, additionally documenting clinical improvement.

Example 3

Additional Clinical Experience—Parkinson's Disease

In the inventor's out-patient neurology practice, in excess of 60 PD patients have been treated with topical apomorphine employing the principles of topical regional neuroaffective (TRNA) therapy in similar fashion as in Example 2. That experience suggests topical apomorphine alleviates clinical symptoms of PD in a measurable way over 85% of the time when patients are treated in the "off-state" and exhibiting such symptoms: tremor, rigidity, postural instability, and reduced spontaneity, among others. Symptom improvement was clinically evident to both the patient and the treating physician within 15 minutes of topical drug application. No appreciable side-effects were noted. Clinical benefit lasted, on the average, 4 hours, with some patients reporting over 10 hours. Formal double-blind, placebo-controlled, cross-over long-term studies are contemplated.

Example 4

TRNA Therapy in Tremor

In the inventor's out-patient neurology practice, approximately 20 patients with tremor have been treated with topical apomorphine in similar fashion as in Example 2. Improvement in tremor not attributed to Parkinson's disease has also been noted with TRNA apomorphine therapy. This has consisted of patients with benign essential/familial tremor as well as tremor associated with Multiple Sclerosis, stroke disease, and degenerative CNS conditions such as cerebellar degeneration.

The inventor treated 5 patients with benign essential tremor. They were either all on their tremor medications at the time or had given up on drug therapy because of side-effects. One 74 yr. old lady (on video), with tremor since age 19, was on 4 meds when the inventor treated her on 3 occasions. She responded dramatically (tremor improved over 70%) each time and is now using the topical apomorphine (1 mg/0.5 ml) 2×/day on a regular basis. All the other patients also responded to 1 mg of apomorphine to varying degrees—anywhere from 30-80% reduction in tremor.

The inventor also treated 3 patients with MS related tremor. They also all responded with 50-80% reduction.

The inventor also treated 2 patients with stroke related tremor. One had been severely affected by tremor and incoordination for over 10 years and she responded dramatically. As of filing, this patient is using it on a regular basis: 1 mg once to twice a day. The other patient also improved but the cost of drug from the compounding pharmacy was prohibitive.

The inventor has treated 2 patients with CNS degeneration related tremor (cerebellar degeneration); one is 46 yr. old female, the other a 20 yr. old male (video taped). As of filing, both responded and are using the cream 2×/day. Both these patients had either failed other drugs or could not tolerate them.

The balance of the tremor patients, 6 patients, were of uncertain etiology. Some of them had components suggestive of early Parkinson's Disease (PD) or tremor predominant PD. In these, the response was present but not as dramatic, 30-50% reduction.

The duration of improvement of tremor in all these patients was on average 4 hours.

Example 5

Dystonia and Torticollis

In the inventor's out-patient neurology practice, several patients with cervical dystonia and torticollis have been observed to improve with topical apomorphine administered in similar fashion as in Example 2. Some of these patients also exhibited improvement in the spasticity that involved aspects of their bodies when present. In patients with significant rigidity and dystonia, the reduction in muscle tone was noticeably accompanied by an overall improved affect and spontaneity. This may be attributed to diminished pain and disability associated with the dystonia but other mechanisms associated with TRNA apomorphine therapy need also to be considered. This phenomenon was also observed in Parkinson's Disease (PD) patients with significant rigidity and motor complications. Improved cognitive abilities and speech was also observed in some of these patients. These observations require further detailed study.

The inventor has treated 3 patients with cervical dystonia and torticollis. One patient was treated three times and she continues to use 1 mg apomorphine twice a day on her own for relief of symptoms. A video exists on this patient. The other two patients also responded to varying degrees that was noted by family members.

When PD was associated with significant rigidity, speech difficulty, and distress (both physically and emotionally), the response appeared to be the most dramatic. All patients reported a "calming and relaxing" effect which was obvious in their facial expressions. Speech was also significantly improved. In the 15 patients the inventor treated in an uncompleted trial (discontinued for reasons other than the treatment), speech, swallow (by video), and cognition were documented as improved. In these 15 patients, active and placebo were given in 5 patients twice and once each for the remaining 10 patient's.

Example 6

Other Applications of TRNA Therapy in Clinical Practice

The inventor has also used topical clonidine and rivastigmine in the form of currently commercially available transdermal patches (Catapress TTS and Exelon patch, respectively) applied to the posterior cervical region (back of the neck at the hairline, "BONATH") to capitalize on the principles of TRNA delivery. These transdermal patches were used in patients clinically unresponsive to the usual methods of treatment with these patches—placement at the usual sites of placement on the body. In placing the transdermal patches at the BONATH, more efficient and effective therapeutic action of these 2 drugs is elicited.

The inventor administered Catapres TTS® 0.1 mg patch at the BONATH on a female patient 52 yr. old who had suffered an intracranial hemorrhage from a ruptured aneurysm. She had uncontrolled central hypertension despite 4 meds and had also failed traditional placement therapy with Catapres. The patch was placed at the BONATH and after 10-15 minutes, the patient's BP dropped from 240/180 to 180/110, still unacceptable but better than what it had been for years. The patient discontinued application of the patch at the BONATH after a period of time due to apparent headaches and remains with severe hypertension which has been deemed incurable by cardiologists and renal physicians.

With respect to the Exelon® patch, the inventor is administering this patch at a dose of 4.6 mg/24 hr patch daily at the BONATH in 6 patients at the time of filing. The patients are tolerating this treatment, but it is still too early to determine the effect on their dementia.

One of the problems with systemic cholinesterase therapy (whether the treatment is with Aricept®, Exelon®, or Reminyl®), is that of GI side-effects (especially nausea and upset stomach). TRNA therapy appears not to have this. But, still the patch was designed for absorption into the bloodstream and may get into the systemic circulation when administered at the BONATH. It is hypothesized that, when made specifically for BONATH application, the dose (particularly tissue penetration) from a patch could be much lower and for a more prolonged delivery, e.g., from about 3 days to about 1 week.

Conclusions Regarding Examples 2-6

These preliminary open-label findings in an outpatient office setting suggest potential utility for apomorphine TRNA therapy in the management of Parkinson's Disease (PD) and other conditions. This form of apomorphine has also been used in benign essential tremor and tremor associated with multiple sclerosis (MS), stroke, and CNS degenerative processes, such as cerebellar degeneration, with similar results. No formal blinded, placebo-controlled studies have been performed at this time; however, preliminary trials using placebo (compounding medium alone) and active drug suggest the validity of the reported findings. A double-blind, placebo-controlled, crossover study is deemed necessary to establish "proof of concept" and confirm these preliminary results.

The examples provided above are not meant to be exclusive. Many other variations of the present invention would be obvious to those skilled in the art, and are contemplated to be within the scope of the appended claims.

The hypotheses of the inventor provided throughout the specification are for possible explanation purposes only, and are not meant to be limiting in any way.

The invention claimed is:

1. A method of treating a disease state or condition in humans comprising administering a therapeutically effective amount of a drug selected from a dopamine agonist useful for topical brainstem de-afferentation therapy to treat a disease state or condition selected from the group consisting of Parkinson's disease, tremor not attributed to Parkinson's disease, dystonia, and torticollis to the back of the neck at the hairline in close proximity to and on the area of skin above the brain stem to provide regional neuro-affective therapy to a human patient, wherein the dopamine agonist is selected from the group consisting of apomorphine, pramipexole, ropinirole, bromocriptine, cabergoline, pergolide, rotigotine, and mixtures of any of the foregoing.

2. The method of claim 1, wherein the drug is apomorphine.

3. The method of claim 1, wherein the disease state or condition is Parkinson's disease.

4. The method of claim 1, further comprising formulating the dopamine agonist in a pharmaceutically acceptable immediate release aqueous-based carrier, and applying a sufficient amount to the BONATH of the human patient such that the onset of clinical effect occurs in less than about 30 minutes.

5. The method of claim 4, wherein the therapeutically effective amount of dopamine agonist is applied as a unit dose comprising from about 0.25 mg to about 4 mg dopamine agonist based on apomorphine, or a therapeutically equivalent amount of another dopamine agonist.

6. The method of claim 5, wherein the carrier is a gel or cream.

7. The method of claim 1, wherein the dopamine agonist is incorporated into a sustained release transdermal delivery system which is cap able of delivering from about 4 mg to about 50 mg of the dopamine agonist through the skin of a human patient over a 24 hour period, the transdermal delivery system being capable of delivering the dopamine agonist in such amounts for a time period from about 1 to about 7 days.

8. The method of claim 7, wherein the transdermal delivery system is selected from the group consisting of a transdermal patch, a transdermal plaster, a transdermal disc, and an iontophoretic transdermal device.

9. The method of claim 1, further comprising formulating the drug in a pharmaceutically acceptable immediate release aqueous-based carrier, and applying a sufficient amount to the BONATH of the human patient such that the onset of clinical effect occurs in less than about 15 minutes.

10. The method of claim 1, wherein the dopamine agonist is selected from the group consisting of apomorphine, ropinorole, rotigotine, pramipexole, and mixtures of any of the foregoing.

11. A method of treating a disease state or condition in humans, comprising administering a therapeutically effective amount of a dopamine agonist to the back of the neck at the hairline in close proximity to and on the area of skin above the brain stem a unit dose comprising from about 0.25 mg to about 4 mg dopamine agonist based on apomorphine, or a therapeutically equivalent amount of another dopamine agonist useful for topical brainstem de-afferentation therapy, to provide regional neuro-affective therapy to a human the patient in need of treatment for Parkinson's disease, tremor not attributed to Parkinson's disease, dystonia and torticollis, wherein the dopamine agonist is selected from the group consisting of apomorphine, pramipexole, ropinirole, bromocriptine, cabergoline, pergolide, rotigotine, and mixtures of any of the foregoing.

12. The method of claim 11, further comprising formulating the dopamine agonist in a pharmaceutically acceptable immediate release aqueous-based carrier, and applying a sufficient amount to the BONATH of the human patient such that the onset of clinical effect occurs in less than about 30 minutes.

13. The method of claim 12, wherein the drug is apomorphine.

14. A method of treating a disease state or condition in humans comprising administering to a human patient a therapeutically effective amount of a dopamine agonist selected from the group consisting of apomorphine, ropinorole, rotigotine, pramipexole, and mixtures of any of the foregoing to the back of the neck at the hairline in close proximity to and on the area of skin above the brain stem to treat a disease state or condition selected from the group consisting of Parkinson's disease, tremor not attributed to Parkinson's disease, dystonia, and torticollis.

15. The method of claim 14, wherein the dopamine agonist is administered in close proximity to and on the area of skin above the brain stem a unit dose, and the dopamine agonist comprises from about 0.25 mg to about 4 mg apomorphine.

16. The method of claim 15, wherein the apomorphine is formulated in a pharmaceutically acceptable immediate release aqueous-based carrier, and a sufficient amount is applied to the to the back of the neck at the hairline in close proximity to and under or on the area of skin above the brain stem of the human patient such that the onset of clinical effect occurs in less than about 30 minutes.

17. The method of claim 14, wherein the dopamine agonist is incorporated into a sustained release transdermal delivery system which is capable of delivering from about 4 mg to about 50 mg of the dopamine agonist through the skin of a human patient over a 24 hour period, the transdermal delivery system being capable of delivering the dopamine agonist in such amounts for a time period from about 1 to about 7 days.

* * * * *